United States Patent
Kuboi

(10) Patent No.: US 12,035,895 B2
(45) Date of Patent: Jul. 16, 2024

(54) GEOMETRIC LIGHT SOURCE APPARATUS WITH DIMMING FEATURES FOR ENDOSCOPE

(71) Applicant: OLYMPUS CORPORATION, Tokyo (JP)

(72) Inventor: Toru Kuboi, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 498 days.

(21) Appl. No.: 17/463,727

(22) Filed: Sep. 1, 2021

(65) Prior Publication Data
US 2021/0393118 A1 Dec. 23, 2021

Related U.S. Application Data

(63) Continuation of application No. PCT/JP2019/011290, filed on Mar. 18, 2019.

(51) Int. Cl.
*A61B 1/06* (2006.01)
*A61B 1/00* (2006.01)
(Continued)

(52) U.S. Cl.
CPC ........ *A61B 1/0669* (2013.01); *A61B 1/00006* (2013.01); *A61B 1/0655* (2022.02);
(Continued)

(58) Field of Classification Search
CPC ............. F21Y 2107/00; F21Y 2107/40; F21V 23/002–006; F21V 19/0015; F21V 29/70;
(Continued)

(56) References Cited

U.S. PATENT DOCUMENTS 6,528,954 B1 * 3/2003 Lys ........................ H05B 45/22
315/158
9,526,144 B2 * 12/2016 Yabe ................... A61B 1/00002
(Continued)

FOREIGN PATENT DOCUMENTS

CN         103431833 A      12/2013
CN         115585412 A  *    1/2023
(Continued)

OTHER PUBLICATIONS

International Search Report dated Jun. 18, 2019 received in PCT/JP2019/011290.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

A light source apparatus includes: a first light source; a second light source configured to emit light having a dimming resolution lower than a dimming resolution of the first light source; a holder configured to hold the first light source and the second light source on a first surface of the holder; a substrate provided to face a second surface of the holder, the second surface being different from the first surface, and a circuit configured to control driving of the first light source and the second light source being mounted on the substrate; a first wiring configured to electrically connect the first light source and the substrate; and a second wiring configured to electrically connect the second light source and the substrate, wherein a length of the first wiring is shorter than a length of the second wiring.

13 Claims, 13 Drawing Sheets

(51) Int. Cl.
*A61B 1/07* (2006.01)
*A61B 1/12* (2006.01)
*F21V 19/00* (2006.01)
*F21V 29/70* (2015.01)

(52) U.S. Cl.
CPC ............ *A61B 1/0661* (2013.01); *A61B 1/128* (2013.01); *F21V 19/0015* (2013.01); *F21V 29/70* (2015.01); *A61B 1/00009* (2013.01); *A61B 1/07* (2013.01)

(58) Field of Classification Search
CPC ..... F21V 19/003; F21V 19/00; A61B 1/0661; A61B 1/07; A61B 1/06; A61B 1/0669; A61B 1/0638; G02B 23/2461
See application file for complete search history.

(56) References Cited

U.S. PATENT DOCUMENTS

| | | | | |
|---|---|---|---|---|
| 10,085,630 | B2* | 10/2018 | Shirota | G02B 27/141 |
| 11,150,546 | B2* | 10/2021 | Nomoto | G03B 21/16 |
| 11,432,706 | B2* | 9/2022 | Talbert | G01J 3/2803 |
| 2009/0040523 | A1 | 2/2009 | Brukilacchio | |
| 2009/0040754 | A1 | 2/2009 | Brukilacchio et al. | |
| 2011/0116261 | A1 | 5/2011 | Brukilacchio et al. | |
| 2012/0106192 | A1 | 5/2012 | Brukilacchio | |
| 2012/0307514 | A1 | 12/2012 | Brukilacchio et al. | |
| 2013/0188388 | A1* | 7/2013 | Jaffe | F21V 9/30 362/580 |
| 2013/0284943 | A1 | 10/2013 | Brukilacchio et al. | |
| 2013/0334440 | A1 | 12/2013 | Brukilacchio | |
| 2014/0022810 | A1* | 1/2014 | Ito | G02B 23/2469 362/277 |
| 2014/0098560 | A1 | 4/2014 | Brukilacchio | |
| 2014/0119006 | A1 | 5/2014 | Brukilacchio et al. | |
| 2015/0267897 | A1 | 9/2015 | Brukilacchio et al. | |
| 2015/0276153 | A1 | 10/2015 | Brukilacchio | |
| 2016/0126698 | A1* | 5/2016 | Nishio | H01S 5/06804 372/34 |
| 2016/0367124 | A1 | 12/2016 | Nishio | |
| 2019/0003660 | A1* | 1/2019 | Jang | F21V 5/04 |
| 2019/0021583 | A1* | 1/2019 | Yoshida | F21V 29/673 |
| 2020/0300451 | A1* | 9/2020 | Ozeki | F21V 29/763 |
| 2021/0010658 | A1* | 1/2021 | Ward | F21V 29/90 |
| 2021/0165153 | A1* | 6/2021 | Shibata | F21V 9/30 |
| 2021/0333532 | A1* | 10/2021 | Whoriskey | F21S 2/005 |
| 2022/0095895 | A1* | 3/2022 | Tabata | G02B 6/0006 |

FOREIGN PATENT DOCUMENTS

| | | |
|---|---|---|
| JP | 2010-067680 A | 3/2010 |
| JP | 2015-039447 A | 3/2015 |
| WO | 2015/005167 A1 | 1/2015 |
| WO | 2015/133528 A1 | 9/2015 |

* cited by examiner

GEOMETRIC LIGHT SOURCE APPARATUS WITH DIMMING FEATURES FOR ENDOSCOPE

This application is a continuation of International Application No. PCT/JP2019/011290, filed on Mar. 10, 2019, the entire contents of which are incorporated herein by reference.

BACKGROUND

The present disclosure relates a light source apparatus for an endoscope.

In the medical field, an endoscope system has been used to observe the inside of a subject. In an endoscope, generally, an insertion unit having flexibility and having an elongated shape is inserted into the subject such as a patient, and the inside of the subject is illuminated from a distal end of the insertion unit by illumination light supplied by a light source device. In the endoscope, an imaging unit at the distal end of the insertion unit receives reflected light of the illumination light to capture an in-vivo image. The in-vivo image captured by the imaging unit of the endoscope is subjected to predetermined image processing in a processing device of the endoscope system, and then is displayed on a display of the endoscope system. A user such as a doctor observes organs of the subject based on the in-vivo image displayed on the display.

As the light source device that emits the illumination light, a light source device is known which includes an L-shaped holder formed by bending a central portion of a flat plate-shaped member at right angle (for example, refer to JP 2010-067680 A). In JP 2010-067680 A, one portion (first portion) of two portions having a bent portion of the holder as a boundary is provided with 3 plurality of light sources. In the first portion, illumination light-emitting surfaces of the light sources are disposed on one surface, and wirings that connect the light sources and a substrate which controls the light emission of the light sources are provided on the other surface. In addition, a Peltier element and a heat radiator are provided in the other portion (second portion), and absorb heat generated by the light sources to release the absorbed heat to the outside. Since the heat of the light sources is released to the outside via the second portion, an increase in the temperature of the light sources is suppressed.

SUMMARY

According to one aspect of the present disclosure, there is provided a light source apparatus including: a first light source; a second light source configured to emit light having a dimming resolution lower than a dimming resolution of the first light source; a holder configured to hold the first light source and the second light source on a first surface of the holder; a substrate provided to face a second surface of the holder, the second surface being different from the first surface, and a circuit configured to control driving of the first light source and the second light source being mounted on the substrate; a first wiring configured to electrically connect the first light source and the substrate; and a second wiring configured to electrically connect the second light source and the substrate, wherein a length of the first wiring is shorter than a length of the second wiring.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, a mode for implementing the present disclosure (hereinafter, referred to as an "embodiment") will be described. In the embodiment, as one example of a system including a light source apparatus for an endoscope according to the present disclosure, a medical endoscope system that captures an in-vivo image of a subject such as a patient will be described. In addition, the disclosure is not limited by the embodiment. Further, in the description of the drawings, the same portions are denoted by the same reference signs.

Figure 1:
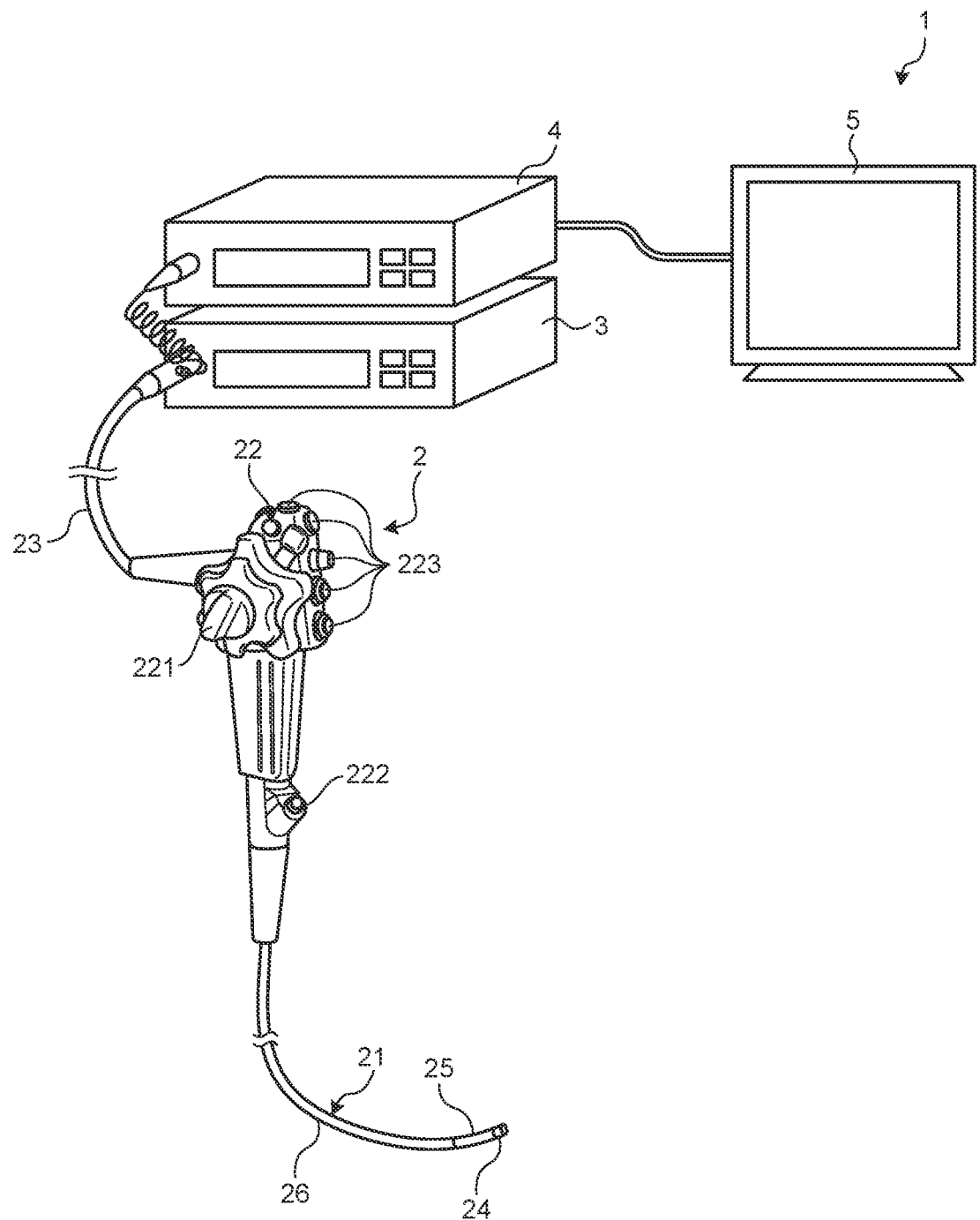
FIG. 1 is a view illustrating a schematic configuration of an endoscope system according to one embodiment.
Figure 2:
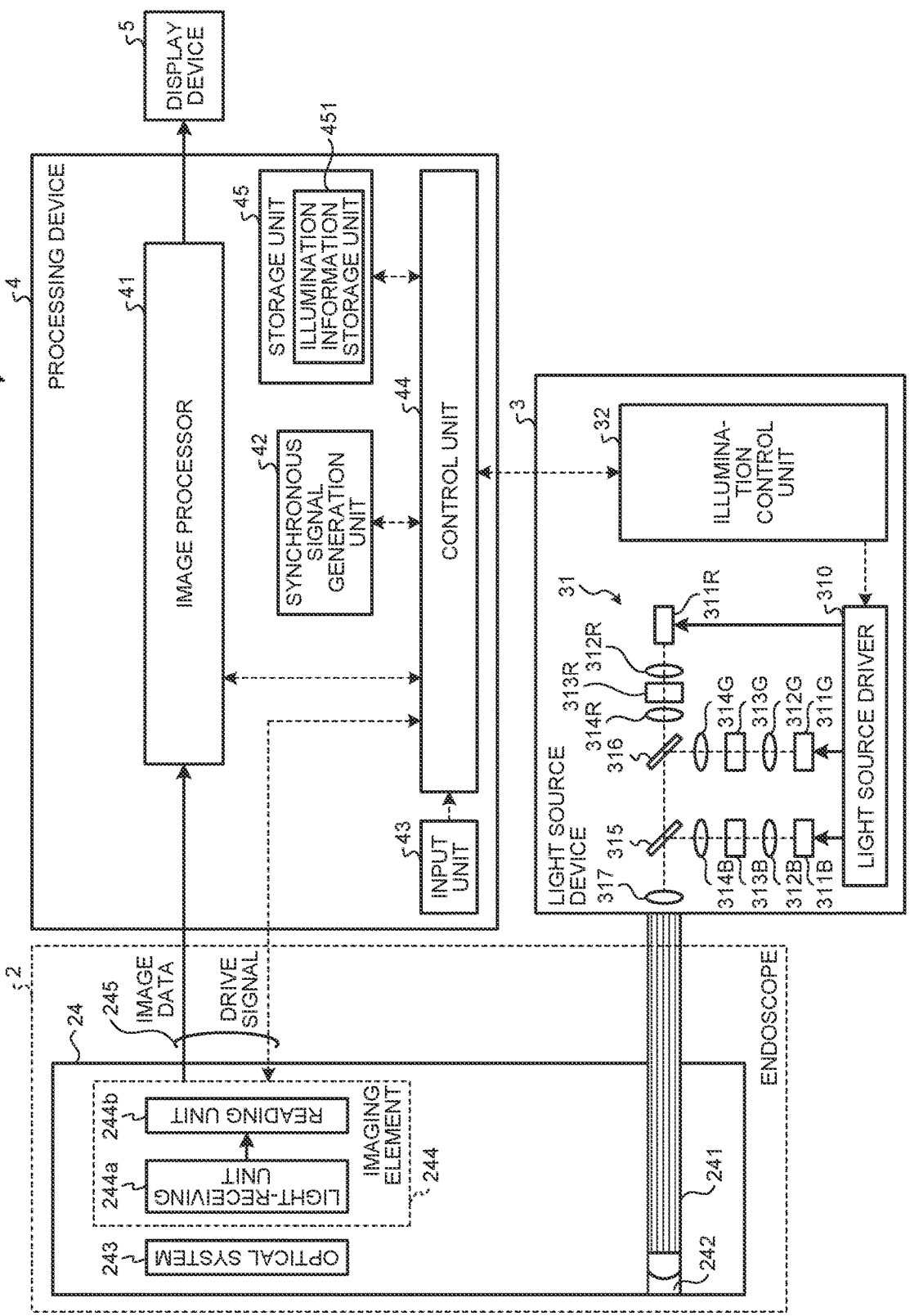
FIG. 2 is a block diagram illustrating a schematic configuration of the endoscope system according to one embodiment.

FIG. 1 is a view illustrating a schematic configuration of an endoscope system according to one embodiment. FIG. 2 is a block diagram illustrating a schematic configuration of the endoscope system according to the embodiment.

An endoscope system 1 illustrated in FIGS. 1 and 2 includes an endoscope 2 that causes a distal end portion to be inserted into a subject, and captures an in-vivo image of the subject; a light source device 3 that generates illumination light to be emitted from a distal end of the endoscope 2; a processing device 4 that performs predetermined signal processing on a signal for the image captured by the endoscope 2, and integrally controls the entire operation of the endoscope system 1; and a display device 5 that displays the in-vivo image generated by the signal processing of the processing device 4.

The endoscope 2 includes an insertion unit 21 having flexibility and having an elongated shape; an operating unit 22 that is connected to a proximal end side of the insertion unit 21, and receives inputs of various operation signals; and a universal cord 23 that extends from the operating unit 22 in a direction different from an extending direction of the insertion unit 21, and contains various cables connected to the light source device 3 and the processing device 4.

The insertion unit 21 includes a distal end portion 24 containing an imaging element 244 in which pixels that receive light and photoelectrically convert the light to generate a signal are arranged two-dimensionally; a bending portion 25 that are formed of a plurality of bending pieces and is bendable; and a long flexible tube portion 26 that is connected to a proximal end side of the bending portion 25 and has flexibility. The insertion unit 21 is inserted in a body cavity of the subject, and allows the imaging element 244 to capture an image of an object such as a biological tissue which is out of reach of external light.

The distal end portion 24 includes a light guide 241 that is formed of a glass fiber or the like, and forms a light-guiding path for the light emitted by the light source device 3; an illumination lens 242 provided at a distal end of the light guide 241; an optical system 243 for condensing light; and the imaging element 244 (imaging unit) that is provided at the image formation position of the optical system 243, and that receives the light condensed by the optical system 243, photoelectrically converts the condensed light into electrical signals, and performs predetermined signal processing thereon.

The optical system 243 is formed of one or a plurality of lenses, and has an optical zoom function of changing the angle of view and a focus function of changing a focal point.

The imaging element 244 photoelectrically converts the light from the optical system 243 to generate electrical signals (imaging signals). Specifically, the imaging element 244 includes a light-receiving unit 244a in which the plurality of pixels are arranged in a matrix pattern, each pixel including a photodiode that, stores an electric charge according to the light quantity, a capacitor that converts the electric charge, which is transferred from the photodiode, into a voltage level, and the like, and each pixel photoelectrically converts the light from the optical system 243 to generate electrical signals, and a reading unit 244b that sequentially reads the electrical signals which are generated by the pixels set arbitrarily as reading targets among the plurality of pixels of the light-receiving unit 244a, and outputs the electrical signals as imaging signals. The imaging element 244 is realized by using, for example, a charge coupled device (CCD) image sensor or a complementary metal oxide semiconductor (CMOS) image sensor.

Incidentally, the endoscope 2 includes a memory that stores an execution program and a control program for enabling the imaging element 244 to execute various operations, or data including identification information of the endoscope 2 (not illustrated). The identification information includes unique information (ID), model year, specification information, a transmission method, and the like of the endoscope 2. In addition, the memory may temporarily store image data and the like generated by the imaging element 244.

The operating unit 22 includes a bending knob 221 that bends the bending portion 25 in an up-down direction and a right-left direction; a treatment tool insertion portion 222 through which a treatment tool such as biopsy forceps, an electric knife, or an examination probe is inserted into the body cavity of the subject; and a plurality of switches 223 which are operation input units that input operation instruction signals for peripheral devices such as an air supply device, a water supply device, and screen display control in addition to the processing device 4. The treatment tool inserted from the treatment tool insertion portion 222 is exposed from an aperture (not illustrated) via a treatment tool channel (not illustrated) of the distal end portion 24.

The universal cord 23 contains at least the light guide 241 and a cable assembly 245 in which one or a plurality of signal lines are bundled. The cable assembly 245 includes a signal line that transmits an imaging signal, a signal line that transmits a drive signal for driving the imaging element 244, and a signal line that transmits and receives information including unique information and the like regarding the endoscope 2 (imaging element 244). Incidentally, in the present embodiment, a configuration will be described in which electrical signals are transmitted using a signal line; however, optical signals may be transmitted or signals are transmitted between the endoscope 2 and the processing device 4 by wireless communication.

Subsequently, a configuration of the light source device 3 will be described. The light source device 3 includes a light source unit 31 and an illumination control unit 32.

The illumination control unit 32 controls the amount of electric power to be supplied to each light source, and controls the drive timing of each light source provided in the light source unit 31 based on a control signal (dimming signal) from a control unit 44. In the present embodiment, the dimming signal is a pulse signal having a predetermined waveform.

The light source unit 31 is formed of a plurality of light sources that emit a plurality of illumination light having different wavelength bands from each other, a plurality of lenses, or the like, and emits illumination light including light of a predetermined wavelength band by the driving of each light source. Specifically, the light source unit 31 includes 3 light source driver 310; a first light source apparatus 311B that emits light of a wavelength band of 390 to 495 nm (blue illumination light); a second light source apparatus 311G that emits light, of a wavelength band of 495 to 590 nm (green illumination light); a third light source apparatus 311R that emits light of a wavelength band of 590 to 750 nm (red illumination light); first lenses (first lenses 312B, 312G, and 312R) that condense the illumination light emitted by each light source; light quantity sensors (light quantity sensors 313B, 313G, and 313R) that detect the light quantities of the illumination light which has passed through the first, lenses; second lenses (second lenses 314B, 314G, and 314R) that condense the illumination light which has passed through the light quantity sensors; a dichroic mirror 315 that refracts the light of the wavelength band emitted by the first light source apparatus 311B, and transmits light of other wavelength bands; a dichroic mirror 316 that refracts the light of the wavelength band emitted by the second light source apparatus 311G, and transmits light of other wavelength bands; and a lens 317 that guides the wavelength, which is emitted by each light source, to the light guide 241. Each of the light source subsystems is realised by using a plurality of semiconductor lasers, a plurality of LED light sources, or the like. The dichroic mirrors 315 and 316 refract the light from the light source apparatus to cause the refracted light to travel on the same optical axis. A diffusion plate is provided in each of the light quantity sensors to diffuse incident illumination light and emit the diffused illumination light. The light quantity sensor acquires a part of light before (or after) the light passes through the diffusion plate, and outputs the light quantity value thereof or outputs an estimated value of the light quantity of light, which is emitted by the light source, from the light quantity value of the acquired light.

The light source driver 310 supplies current to each of the light source subsystems under the control of the illumination control unit 32 to cause the light sources to emit light.

The light source unit 31 emits illumination light of a single color to the outside by causing the first light source apparatus 311B, the second light source apparatus 312G, or the third light source apparatus 311R to emit illumination light, or emits while illumination color by causing all the light sources to emit light.

Figure 3:
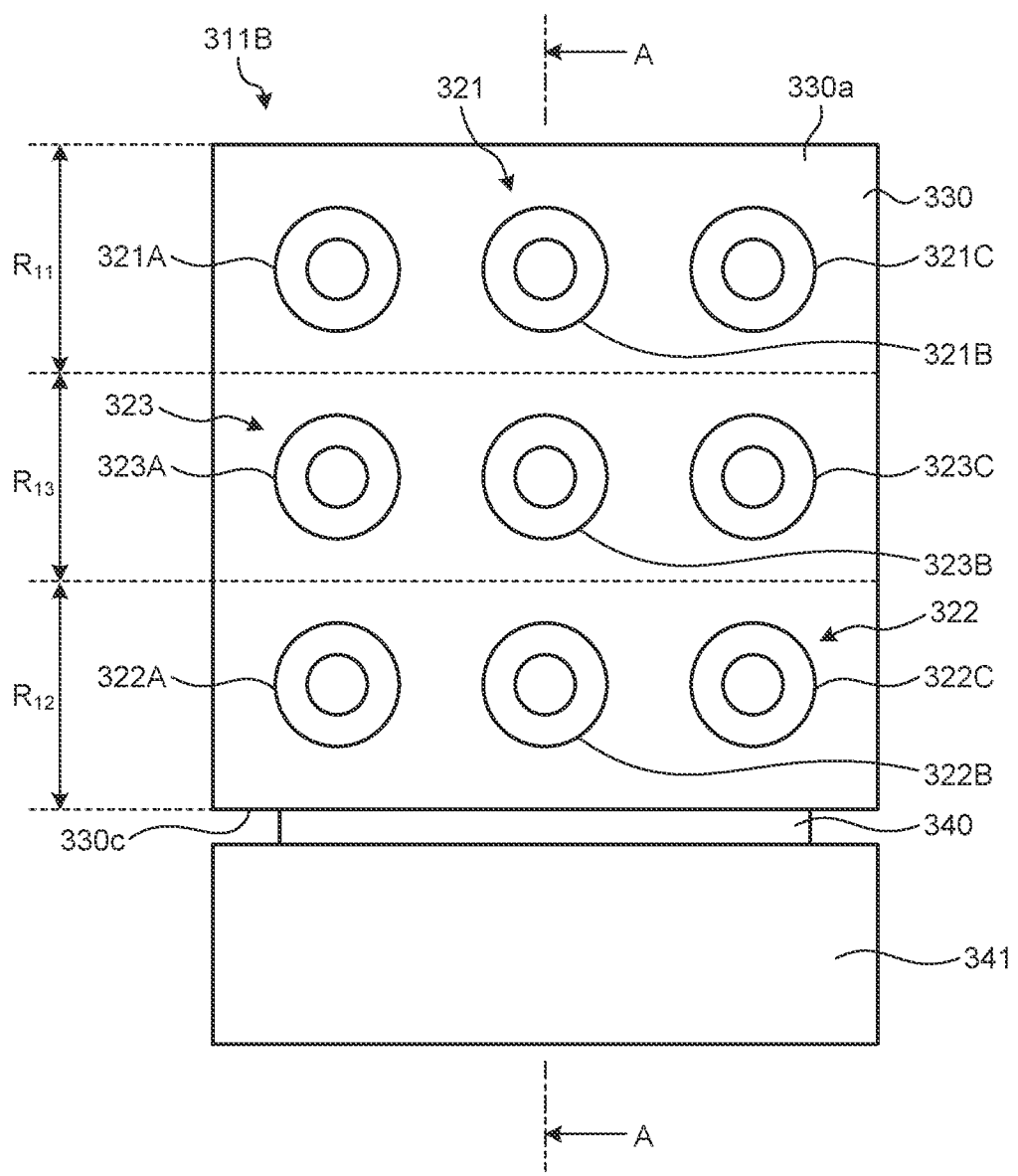
FIG. 3 is a view describing a configuration of a light source apparatus of a light source device provided in the endoscope system according to one embodiment.
Figure 4:
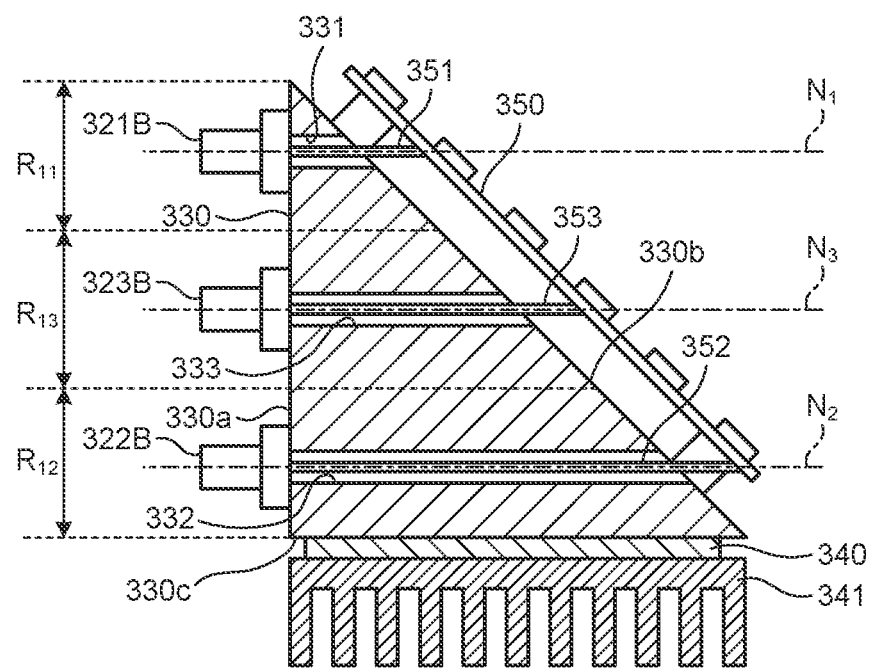
FIG. 4 is a cross-sectional view taken along line A-A illustrated in FIG. 3.

Here, a configuration of each of the light source subsystems will be described with reference to FIGS. 3 and 4. FIG. 3 is a view describing a configuration of the light source apparatus of the light source device provided in the endoscope system according to one embodiment. FIG. 4 is a cross-sectional view taken along line A-A illustrated in FIG. 3. In each of the light source subsystems, a plurality of light sources are provided at the same disposition. Hereinafter, a configuration of the first light source apparatus 311B will be described. Incidentally, the second light source apparatus 311G and the third light source apparatus 311B also have the same configuration.

The first light source apparatus 311B includes a first light source 321 formed of s set of three light sources (light sources 321A to 321C); a second light source 322 formed of a set of three light sources (light sources 322A to 322C); a third light source 323 formed of a set of three light sources (light sources 323A to 323C); a holder 330 that holds each light source; a Peltier element 340 attached to the holder 330; a heat sink 341; and a substrate 350 on which a circuit that controls the light emission of each light source is formed. The first light source 321 to the third light source 323 each emit the same color component (wavelength: 390 to 495 nm).

Each light source of the first light source 321, the second light source 322, and the third light source 323 is formed of a semiconductor laser.

The dimming resolution of the first light source 321 is higher than at least the dimming resolution of the second light source 322. In other words, the dimming resolution of the second light source 322 is lower than the dimming resolution of the first light source 321. The dimming resolution referred to here is defined by the step size of a dimming value in a control circuit, and refers to the adjustment width of the emission interval of light or the adjustment width of the light quantity at that time. For example, it may be said that the smaller the adjustment width corresponding to the emission interval is, the higher the dimming resolution is. The first light source 321 has a smaller adjustment width than the second light source 322, and may be finely adjusted. Incidentally, the maximum light quantity to be emitted by the light source of the first light source 321 may be smaller than the maximum light quantity to be emitted by the light source of the second light source 322.

In addition, the dimming resolution of the third light source 323 is from the dimming resolution of the second light source 322 to the dimming resolution of the first light source 321.

Here, the dimming resolution will be described with reference to FIGS. 5A, 5B, 6A, and 6B. Incidentally, in FIGS. 5A, 5B, 6A, and 6B, an example will be described in which when the pulse has risen, illumination is turned on, and when the pulse has fallen and the height of the pulse (pulse height) has become zero, illumination is turned off. In addition, the higher the pulse height is, the larger the light emission intensity is.

Figure 5A:
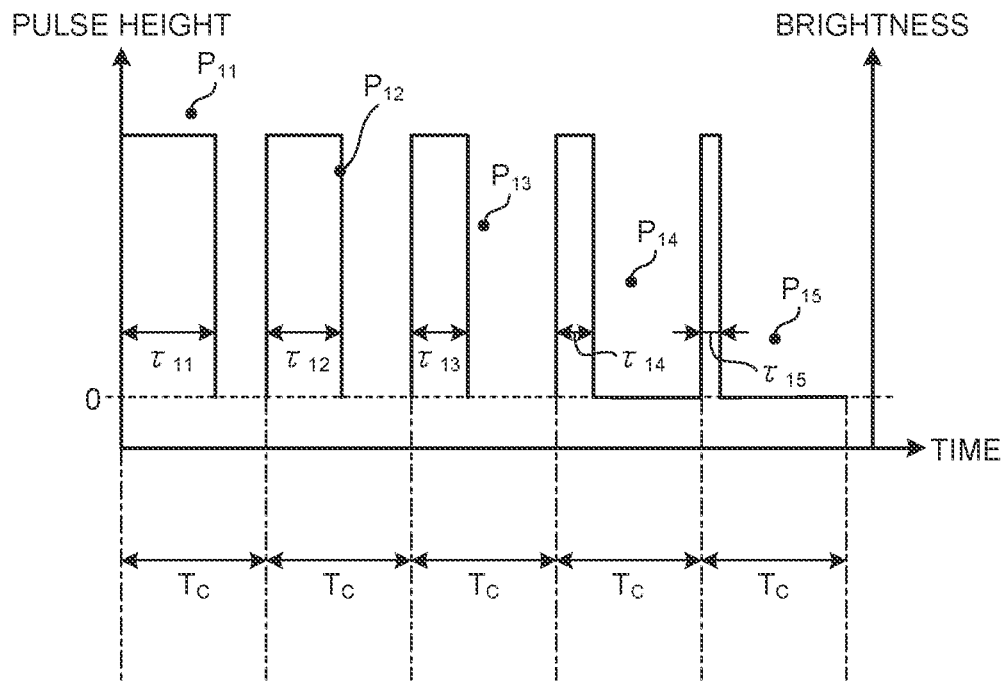
FIG. 5A is a graph describing the dimming resolution of a light source.
Figure 5B:
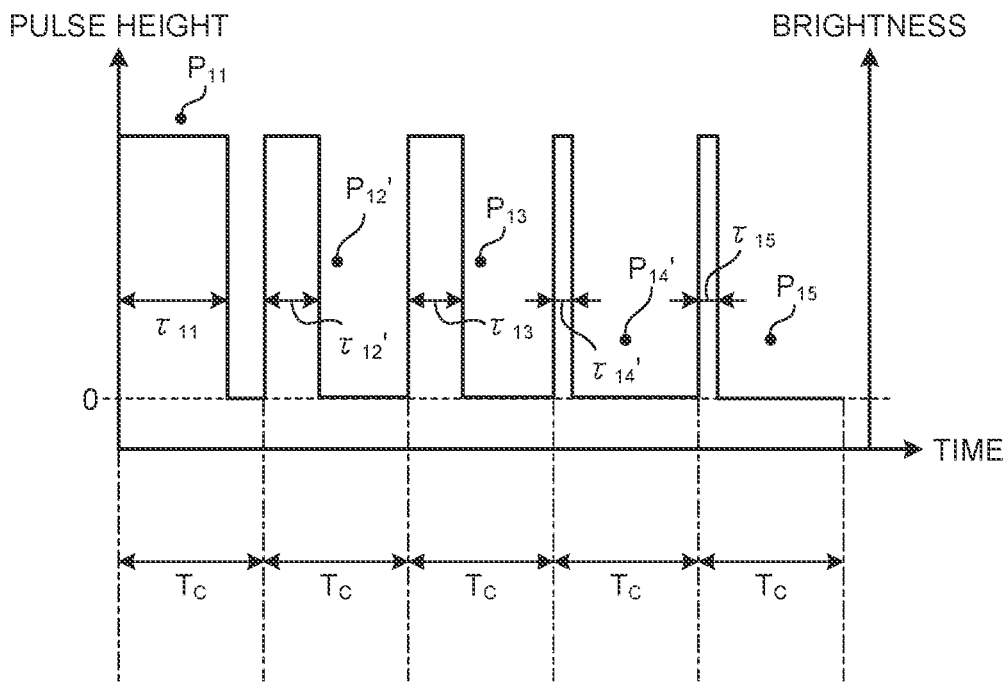
FIG. 5B is a graph describing the dimming resolution of the light source.

FIGS. 5A and 5B are views describing the dimming resolution of the light source, and are views describing dimming resolutions at which the adjustment widths of the emission interval of light are different. FIG. 5B illustrates an example of a dimming resolution lower than the dimming resolution illustrated in FIG. 5A. In FIG. 5A, the period that is a control period corresponding to one irradiation of illumination light is set to $T_c$, and the time width (pulse width) from rising to falling is set to $\tau$ ($\tau_{11}$ to $\tau_{15}$). When light is emitted with the time width $\tau$ set in each period, the brightness also changes in each period. Specifically, in the example of FIG. 5A in which the pulse widths decrease sequentially, brightnesses ($P_{11}$, $P_{12}$, $P_{13}$, $P_{14}$, and $P_{15}$) in the periods $T_c$ also decrease with the elapse of time. Incidentally, the brightnesses $P_{11}$ to $P_{15}$ indicate brightnesses in the periods, and do not indicate brightnesses at times corresponding to the time axis. At this time, the dimming resolution in the cases illustrated in FIGS. 5A and 5E is the adjustment width of the time width (pulse width). The minimum adjustment width at a high dimming resolution (FIG. 5A) is set to $\Delta t$, and the minimum adjustment width at a low dimming resolution (FIG. 5B) is set to $\Delta t'$. Here, an example of $\Delta t'=2 \times \Delta t$ will be described. The minimum adjustment width $\Delta t$ at a high dimming resolution corresponds to, for example, a difference between the pulse width $\tau_{11}$ in the initial period $T_c$ illustrated in FIG. 5A and the pulse width $\tau_{12}$ in the following period $T_c$. In FIG. 5A, all of $\tau_{11}-\tau_{12}$, $\tau_{12}-\tau_{13}$, $\tau_{13}-\tau_{14}$, and $\tau_{14}-\tau_{15}$ have the same value, and are $\Delta t$ or more and less than $\Delta t'$. In addition, for example, $\tau_{11}-\tau_{13}$ is $\Delta t'$ or more.

In FIG. 5A, the time widths decrease with the elapse of time in order, but as long as the set light quantity is reached in a predetermined number of periods, the time widths are not limited to decreasing or increasing in order, and an arbitrary time width may be set in each period.

In addition, in the example of FIG. 5B in which the dimming resolution is low, the time widths (pulse widths) change in order of $\tau_{11}$, $\tau_{12}'$ ($=\tau_{13}$), $\tau_{13}$, $\tau_{14}'$ ($=\tau_{15}$), and $\tau_{15}$. Incidentally, the period $T_c$ is the same as that of FIG. 5A. In FIG. 5B, since $\Delta t'$ is larger than $\tau_{11}-\tau_{12}$ ($\Delta t$), the transition from the pulse width $\tau_{11}$ to the pulse width $\tau_{12}$ illustrated in FIG. 5A cannot be made. For this reason, in the second period, the pulse width is set to the pulse width $\tau_{12}'$ ($=\tau_{13}$) ($\tau_{11}-\tau_{12}' \geq \Delta t'$). Similarly, since $\Delta t'$ is larger than $\tau_{13}-\tau_{14}$ ($\Delta t$), the transition from the pulse width $\tau_{13}$ to the pulse width $\tau_{14}$ illustrated in FIG. 5A cannot be made. For this reason, in the fourth period, the pulse width is set to the pulse width $\tau_{14}'$ ($=\tau_{15}$) ($\tau_{13}-\tau_{14}' \geq \Delta t'$). The light source having a low dimming resolution has a step size larger than the step size of the pulse width of FIG. 5A (refer to FIG. 5B). In the example illustrated in FIG. 5B, in two consecutive periods, illumination light having the same brightness (for example, $P_{12}'$ and $P_{13}$, $P_{14}'$ and $P_{15}$) is emitted. As a result, the light source having a low dimming resolution has a larger difference in light quantity (minimum difference in light quantity) between the periods than when the light source having a high dimming resolution is used.

Figure 6A:
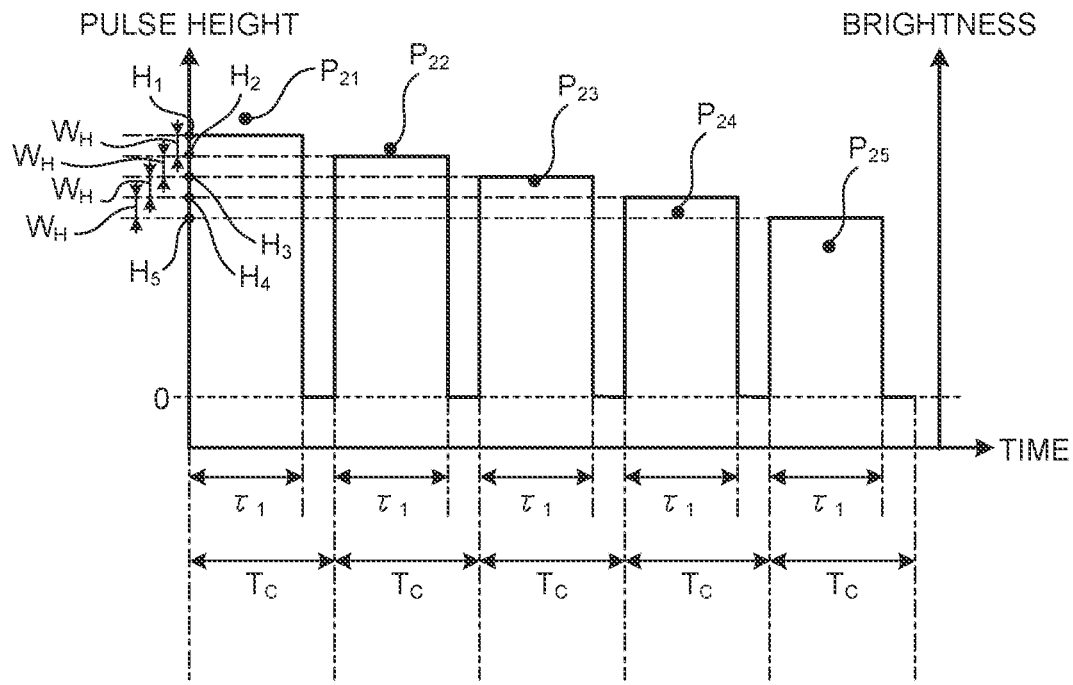
FIG. 6A is a graph describing the dimming resolution of a light source.
Figure 6B:
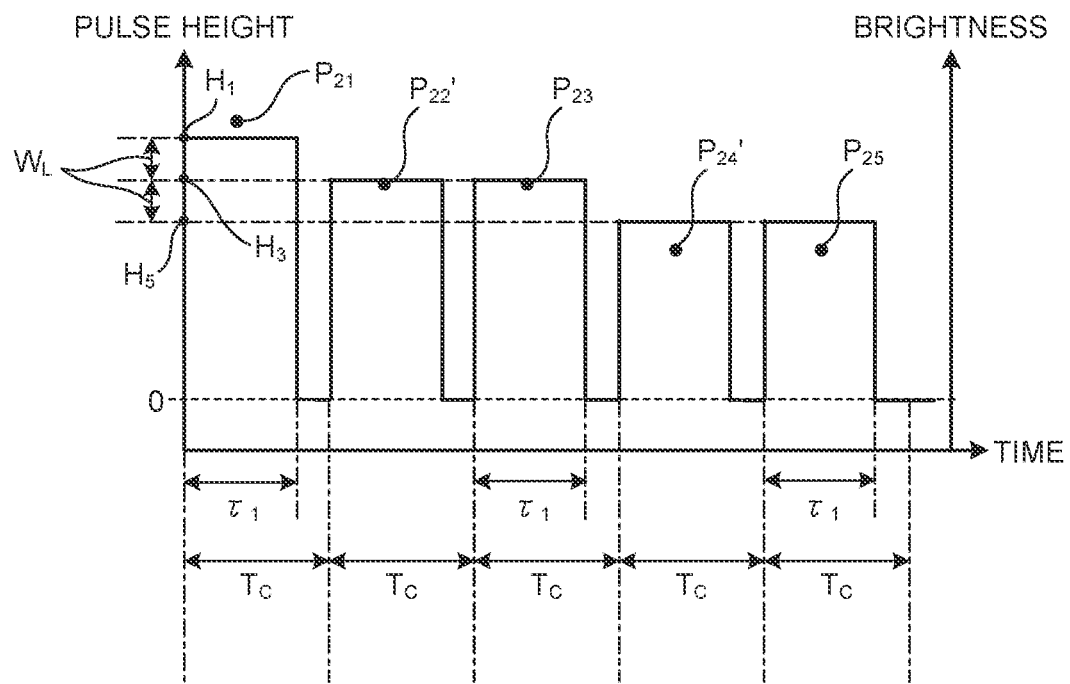
FIG. 6B is a graph describing the dimming resolution of the light source.

FIGS. 6A and 6B are views describing the dimming resolution of the light source, and are views describing dimming resolutions at which the adjustment widths of the light quantity are different. FIG. 6B illustrates an example of a dimming resolution lower than the dimming resolution illustrated in FIG. 6A. In FIG. 6A, the width of a pulse height corresponding to the adjustment width of the light quantity is set to $W_H$. In addition, in FIG. 6B, the width of a pulse height corresponding to the adjustment width of the light quantity is set to $W_L$ ($<W_H$). Incidentally, the period of FIGS. 6A and 6B is set to the period $T_c$ illustrated in FIG. 5A, and the pulse width is set to the pulse width $\tau_1$. In FIG. 6A, the irradiation time is controlled by the pulse width $\tau_1$ for each period $T_c$. In the periods $T_c$, the pulse heights differ by the width $W_H$ with the elapse of time. Specifically, the pulse heights decrease sequentially as the periods proceed ($H_1 > H_2 > H_3 > H_4 > H_5$). The brightness in each period also changes according to a change in pulse height. Specifically, in the example of FIG. 6A in which the pulse heights decrease sequentially, brightnesses ($P_{21}$, $P_{22}$, $P_{23}$, $P_{24}$, and $P_{25}$) in the periods $T_c$ also decrease with the elapse of time. Incidentally, the brightnesses $P_{21}$ to $P_{25}$ indicate brightnesses in the periods $T_c$, and do not indicate brightnesses at times corresponding to the time axis.

Meanwhile, the light source having a low dimming resolution (refer to FIG. 6B) emits illumination light having the same brightness (in FIG. 6B, $P_{22}' = P_{23}$, $P_{24}' = P_{25}$) in two consecutive periods. As a result, the light source having a low dimming resolution has a larger difference in light quantity (minimum difference in light quantity) between the periods than when the light source having a high dimming resolution is used.

Here, in both cases of a case where the light source is used which has a low dimming resolution at which the adjustment width of the pulse width is small and a case where the light source is used which has a low dimming resolution at which the adjustment width of the light quantity (width of the pulse height) is small, for example, in the cases of FIGS. 5A and 5B and FIGS. 6A and 6B, the total illuminance (overall brightness) over a plurality of periods is smaller than that of the light source having a high dimming resolution, so that a larger output than the light source having a high dimming resolution or an increase in the number of the light sources is required.

The holder 330 is a solid member (excluding through-holes to be described later) having a triangular prismatic shape. The first light source 321, second light source 322, and the third light source 323 are arranged on the same surface (surface 330a in the present embodiment) of the holder 330.

In addition, the holder 330 is provided with a first communication portion 331 that allows the surface 330a on which the first light source 321 is arranged and a surface 330b facing the substrate 350 to communicate with each other, a second communication portion 332 that allows the surface 330a on which the second light source 322 is arranged and the surface 330b to communicate with each other, and a third communication portion 333 that allows the surface 330a on which the third light source 323 is arranged and the surface 330b to communicate with each other.

The surface 330b intersects with normal lines $N_1$ to $N_3$ of the surface 330a. The normal line $N_1$ is a straight line passing through an optical axis (center of the arrangement position) of the light source 321A (or the light source 321B or 321C) and extending perpendicular to the surface 330a. The normal line $N_2$ is a straight line passing through an optical axis (center of the arrangement position) of the light source 322A (or the light source 322B or 322C) and extending perpendicular to the surface 330a. The normal line $N_3$ is a straight line passing through an optical axis (center of the arrangement position) of the light source 323A (or the light source 323B or 323C) and extending perpendicular to the surface 330a. The normal lines $N_1$ to $N_3$ are parallel to each other.

The first communication portions 331 each have a hole shape extending in a direction of the normal line $N_1$ of the surface 330a. Similarly, the second communication portions 332 each have a hole shape extending in a direction of the normal line $N_2$ of the surface 330a. The third communication portions 333 each have a hole shape extending in a direction of the normal line $N_3$ of the surface 330a.

A first wiring 351 connecting the first light source 321 and the substrate 350 is inserted into the first communication portion 331. A second wiring 352 connecting the second light source 322 and the substrate 350 is inserted into the second communication portion 332. A third wiring 353 connecting the third light source 323 and the substrate 350 is inserted into the third communication portion 333.

n the holder 330, the surface 330b is inclined with respect to the surface 330a (refer to FIG. 4). For this reason, the length of the first communication portion 331 in the direction of the normal line $N_1$ (central axis direction of the hole) is smaller than the length of the second communication portion 332 in the direction of the normal line $N_2$.

In addition, the substrate 350 is disposed parallel to the surface 330b.

From the length of the first communication portion 331, the length of the second communication portion 332, and the disposition of the substrate 350, the length of the first wiring 351 connecting the first light source 321 and the substrate 350 is shorter than the length of the second wiring 352.

In the first light source apparatus 311B, the first light source 321, the third light source 323, and the second light source 322 are disposed in order of distance from a surface 330c on which the Peltier element 340 and the heat sink 341 are provided. This order is the decreasing order of the dimming resolution. In addition, when the holder 330 is divided into three equal sections by planes parallel to the surface 330c in a direction orthogonal to the planes, the volume of a region $R_{11}$ in which the first light source 321 is arranged is smaller than the volume of a region $R_{12}$ in which the second light source 322 is arranged. In addition, heat that has diffused in a region $R_{13}$ is conducted to the Peltier element 340 via the region $R_{12}$.

Figure 7:
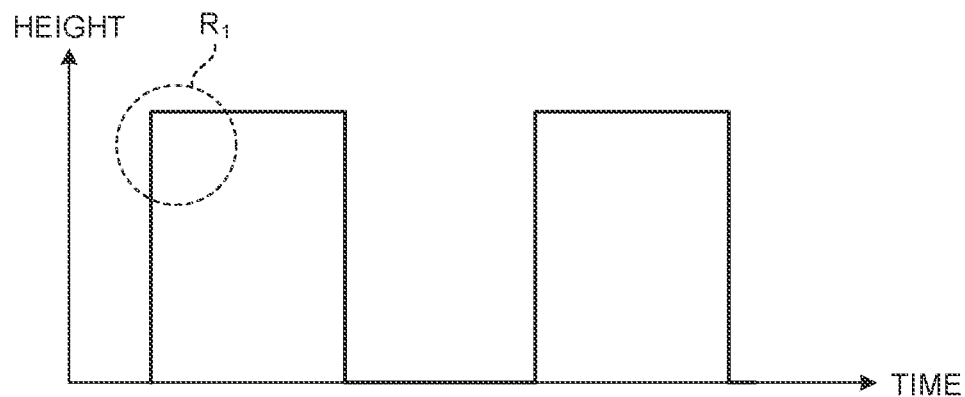
FIG. 7 is a graph describing a pulse signal that controls the emission of the light source in the endoscope system according to the embodiment.
Figure 8:
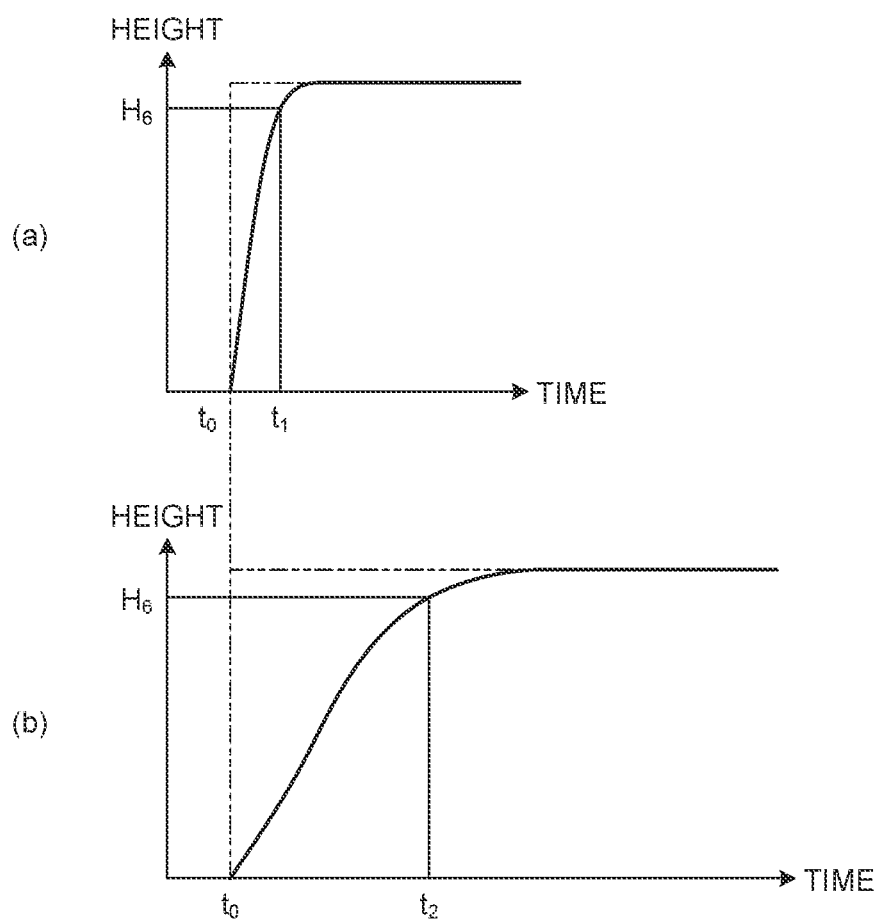
FIG. 8 is a graph describing the waveforms of the pulse signal in a region $R_1$ illustrated in FIG. 7.
Figure 9:
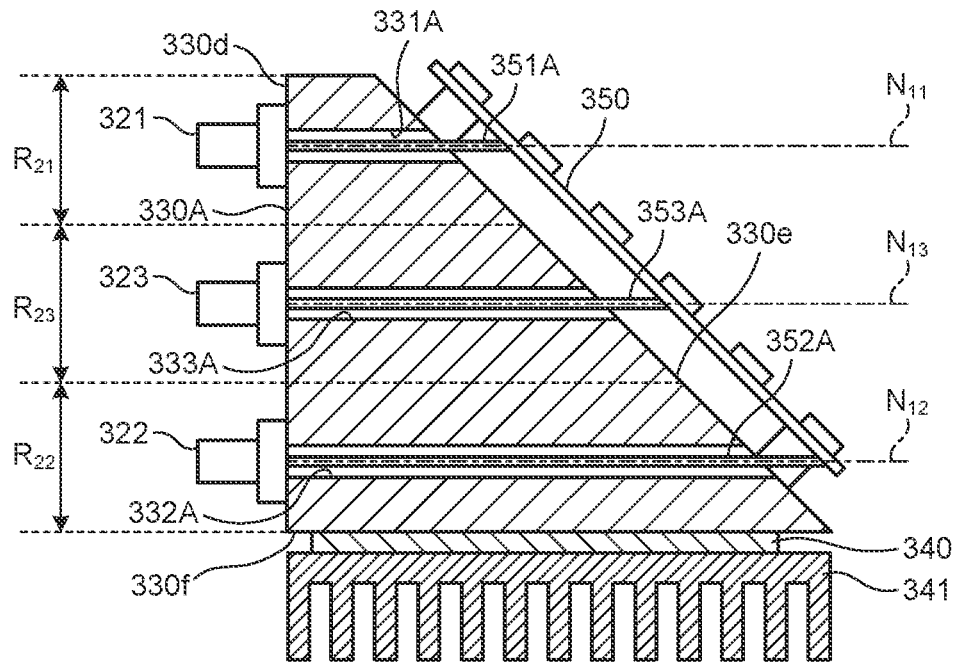
FIG. 9 is a view describing a configuration of main parts of a light source apparatus of a light source device provided in an endoscope system according to a first modification example of the embodiment.

Here, the length of the wiring and a pulse signal to be transmitted will be described with reference to FIGS. 7 and 8. FIG. 7 is a graph describing a pulse signal that controls the emission of the light source in the endoscope system according to the embodiment. FIG. 9 is a graph describing the waveforms of the pulse signal in a region $R_1$ illustrated in FIG. 7.

The pulse signal is a rectangular wave of which the height changes steeply at predetermined time intervals (refer to FIG. 7). In this case, when the wiring is long, blunting occurring in the rectangular wave is large. When the blunting occurs particularly at the time of rising of the pulse, the blunting affects the emission timing of light or the light quantity. For example, if the blunting is small when the pulse has risen at time $t_0$, a predetermined height $H_6$ is reached at time $t_1$ (refer to (a) of FIG. 8). Meanwhile, when the blunting is large, the predetermined height $H_6$ is reached at time $t_2$ ($>t_1$) (refer to (b) of FIG. 8). Particularly, in the first light source 321 in which the step size of the pulse is smaller than that of the second light source 322, the influence of the blunting on the light emission is large. For example, when the falling time is reached before the pulse rises to the height $H_6$, the light emission is controlled by a rectangular wave that does not reach the height $H_6$. Meanwhile, in the present embodiment, the influence of blunting is reduced by shortening the first wiring 351.

A heat absorption side of the Peltier element 340 is disposed on the surface 330c of the holder 330, and a heat generation side thereof is disposed on the heat sink 341. Heat generated by the first light source 321, the second light source 322, and the third light source 323 is conducted to the Peltier element 340 via the holder 330, and is released to the outside via the heat sink 341. At this time, the heat quantity generated by the first light source 321 may be smaller than the heat quantity generated by the second light source 322 due to the light quantity to be emitted. Due to the shape of the holder 330, the volume in which heat is diffused is smaller on a first light source 321 side than on a second light source 322 side, but the heat may be appropriately released to the outside due to the above-described heat quantities.

Next, a configuration of the processing device 4 will be described. The processing device 4 includes an image processor 41, a synchronous signal generation unit 42, an input unit 43, the control unit 44, and a storage unit 45.

The image processor 41 receives image data of illumination light of each color, which is captured by the imaging element 244, from the endoscope 2. When the image processor 41 receives analog image data from the endoscope 2, the image processor 41 performs A/D conversion on the analog image data to generate a digital imaging signal. In addition, when the image processor 41 receives image data as an optical signal from the endoscope 2, the image processor 41 performs photoelectric conversion on the image data to generate a digital image signal.

The image processor 41 performs predetermined image processing on the image data received from the endoscope 2 to generate an image, and outputs the image to the display device 5. Here, the predetermined image processing includes synchronization processing, gradation correction processing, color correction processing, and the like. The synchronization processing is a process of synchronizing R image data based on image data generated by the imaging element 244 when the light source unit 31 irradiates the R illumination light, G image data based on image data generated by the imaging element 244 when the light source unit 31 irradiates the G illumination light, and B image data based on image data generated by the imaging element 244 when the light source unit 31 irradiates the B illumination light. The gradation correction processing is a process of performing gradation correction on the image data. The color correction processing is a process of performing color correction on the image data. The image processor 41 generates a processed imaging signal (hereinafter, also referred to simply as an imaging signal) including an in-vivo image generated by the above-described image processing. Incidentally, the image processor 41 may perform gain adjustment according to the brightness of the image. The image processor 41 is formed of a general-purpose processor such as a central processing unit (CPU) or a dedicated processor such as various arithmetic circuits, for example, an application specific integrated circuit (ASIC), which execute a specific function.

In addition, the image processor 41 may be configured to include a frame memory that holds the R image data, the G image data, and the B image data.

The synchronous signal generation unit 42 generates a clock signal (synchronous signal) serving as a reference for the operation of the processing device 4, and outputs the generated synchronous signal to the light source device 3, the image processor 41, the control unit 44, and the endoscope 2. Here, the synchronous signal generated by the synchronous signal generation unit 42 includes a horizontal synchronous signal and a vertical synchronous signal.

For this reason, the light source device 3, the image processor 41, the control unit 44, and the endoscope 2 operate in synchronization with each other by the generated synchronous signal.

The input unit 43 is realized by using a keyboard, a mouse, a switch, or a touch panel, and receives inputs of various signals such as an operation instruction signal for instructing the operation of the endoscope system 1. Incidentally, the input unit 43 may include a switch provided in the operating unit 22, or a portable terminal such as an external tablet computer.

The control unit 44 performs drive control of components including the imaging element 244 and the light source device 3, the control of input and output of information to and from the components, and the like. The control unit 44 refers to control information data for imaging control (for example, reading timing and the like) that is stored in the storage unit 45, and transmits the control information data as a drive signal to the imaging element 244 via a predetermined signal line included in the cable assembly 245. The control unit 44 is formed of a general-purpose processor such as a CPU or a dedicated processor such as various arithmetic circuits, for example, an ASIC, which execute a specific function. The storage unit 45 stores various programs for operating the endoscope system 1 and data including various parameters and the like required for the operation of the endoscope system 1. In addition, the storage unit 45 stores identification information of the processing device 4. Here, the identification information includes unique information (ID), model year, specification information, and the like of the processing device 4. In addition, the storage unit 45 includes an illumination information storage unit 451 that stores information regarding the disposition and the like of the light sources provided in the light source device 3. The illumination information storage unit 451 stores a light emission pattern of the light sources according to, for example, a set light quantity (in this case, the light quantity of illumination light emitted by the light source device 3).

In addition, the storage unit 45 stores various programs including an image acquisition processing program for executing an image acquisition processing method of the processing device 4. The various programs may be recorded and widely distributed in a computer-readable recording medium such as a hard disk, a flash memory, a CD-ROM, a DVD-ROM, or a flexible disk. Incidentally, the above-described various programs may also be acquired by downloading via a communication network. The communication network referred to here is realized by, for example, the existing public network, a local area network (LAN), a wide area network (WAN), or the like, and may be wired or wireless.

The storage unit 45 having the above configuration is realized by using a read only memory (ROM) in which various programs and the like are installed in advance and a RAM or a hard disk that stores arithmetic parameters, data, and the like of each process.

The display device 5 displays a display image corresponding to the image signal received from the processing device 4 (image processor 41) via a video cable. The display device 5 is formed of a liquid crystal monitor, an organic electroluminescence (EL) monitor, or the like.

In the embodiment described above, the Peltier element 340 and the heat sink 341 are provided on the surface 330c of the holder 330 having a triangular prismatic shape, and the first light source 321, the third light source 323, and the second light source 322 are arranged in decreasing order of the dimming resolution from a side distant from the surface 330c. In the present embodiment, due to the shape of the holder 330 and the order of arrangement of the light sources described above, heat generated by each light source may be efficiently diffused in the holder 330, and radiated to the outside via the Peltier element 340 and the heat sink 341. Accordingly, the temperatures of the light sources (the first light source 321, the second light source 322, and the third light source 323) may be maintained uniform. In addition, according to the present embodiment, the length of the wiring connecting the first light source 321 and the substrate 350 is shortened, so that the occurrence of blunting of the rectangular wave of the pulse may be suppressed, and the light emission of the light sources may be controlled with high accuracy.

Next, a first modification example of the embodiment will be described with reference to FIG. 9. FIG. 9 is a view describing a configuration of main parts of a light source apparatus of a light source device provided in an endoscope system according to the first modification example of the embodiment. The endoscope system according to the first modification example has the same configuration, except that the configuration of the holder in the light source device 3 of the endoscope system 1 described above is changed. Hereinafter, a configuration of a holder which is different from the configuration of the above-described embodiment will be described. Hereinafter, the configuration of the holder in the first light source apparatus 311B will be described, and similar to the embodiment, the same holder may also be arranged in the second light source apparatus 311G and the third light source apparatus 311R.

The first light source apparatus 311B according to the first modification example includes the first light source 321 formed of a set of three light sources (light sources 320A to 320C); the second light source 322 formed of a set of three light sources (light sources 321A to 321C); the third light source 323 formed of a set of three light sources (light sources 322A to 322C); a holder 330A that holds each light source; the Peltier element 340 attached to the holder 330A; the heat sink 341; and the substrate 350 on which a circuit that controls the light emission of each light source is formed.

The holder 330A is a rectangular prismatic member having a trapezoidal bottom surface. The first light source 321, second light source 322, and the third light source 323 are arranged on the same surface 330d of the holder 330A.

In addition, the holder 330A is provided with a first communication portion 331A that allows the surface 330d on which the first light source 321 is arranged and a surface 330e facing the substrate 350 to communicate with each other, a second communication portion 332A that allows the surface 330d on which the second light source 322 is arranged and the surface 330e to communicate with each other, and a third communication portion 333A that allows the surface 330d on which the third light source 323 is arranged and the surface 330e to communicate with each other.

The surface 330e intersects with normal lines $N_{11}$ to $N_{13}$ of the surface 330d. The normal line $N_{11}$ is a straight line passing through the optical axis (center of the arrangement position) of the light source 321A (or the light source 321B or 321C) and extending perpendicular to the surface 330d. The normal line $N_{12}$ is a straight line passing through the optical axis (center of the arrangement position) of the light source 322A (or the light source 322B or 322C) and extending perpendicular to the surface 330d. The normal line $N_{13}$ is a straight line passing through the optical axis (center of the arrangement position) of the light source 323A (or the light source 323B or 323C) and extending perpendicular to the surface 330d. The normal lines $N_{11}$ to $N_{13}$ are parallel to each other.

The first communication portions 331A each have a hole shape extending in a direction of the normal line $N_{11}$ of the surface 330d. Similarly, the second communication portions 332A each have a hole shape extending in a direction of the normal line $N_{12}$ of the surface 330d. The third communication portions 333A each have a hole shape extending in a direction of the normal line $N_{13}$ of the surface 330a.

A first wiring 351A connecting the first light source 321 and the substrate 350 is inserted into the first communication portion 331A. A second wiring 352A connecting the second light source 322 and the substrate 350 is inserted into the second communication portion 332A. A third wiring 353A connecting the third light source 323 and the substrate 350 is inserted into the third communication portion 333A.

In the holder 330A, the surface 330e is inclined with respect to the surface 330d (refer to FIG. 9). For this reason, the length of the first communication portion 331A in the direction of the normal line $N_{11}$ (central axis direction of the hole) is smaller than the length of the second communication portion 332A in the direction of the normal line $N_{12}$.

In addition, the substrate 350 is disposed parallel to the surface 330e.

From the length of the first communication portion 331A, the length of the second communication portion 332A, and the disposition of the substrate 350, the length of the first wiring 351A connecting the first light source 321 and the substrate 350 is shorter than the length of the second wiring 352A. Also in the first modification example, since the first wiring 351A is shorter than the second wiring 352A, and the third wiring 353A, the influence of blunting is small.

In the first light source apparatus 311B, the first light source 321, the third light source 323, and the second light source 322 are disposed in order of distance from a surface 330f on which the Peltier element 340 and the heat sink 341 are provided. This order is the decreasing order of the dimming resolution. In addition, when the holder 330A is divided into three equal sections by planes parallel to the surface 330f in a direction orthogonal to the planes, the volume of a region $R_{21}$ in which the first light source 321 is arranged is smaller than the volume of a region $R_{22}$ in which the second light source 322 is arranged.

Heat that has diffused in a region $R_{21}$ is absorbed by the Peltier element 340 via the regions $R_{22}$ and $R_{23}$. In addition, heat that has diffused in the region $R_{23}$ is absorbed by the Peltier element 340 via the region $R_{22}$.

The heat absorption side of the Peltier element 340 is disposed on the surface 330f of the holder 330A, and the heat generation side thereof is disposed on the heat sink 341.

Heat generated by the first light source 321, the second light source 322, and the third light source 323 is absorbed by the Peltier element 340 via the holder 330A, and is released to the outside via the heat sink 341. Due to the shape of the holder 330A, the volume in which heat is diffused is smaller on the first light source 321 side than on the second light source 322 side.

In the first modification example described above, the Peltier element 340 and the heat sink 341 are provided on the surface 330f of the holder 330A having a rectangular prismatic shape, and the first light source 321, the third light source 323, and the second light source 322 are arranged in decreasing order of the dimming resolution from a side distant from the surface 330f. In the first modification example, due to the shape of the holder 330A and the order of arrangement of the light sources described above, heat generated by each light source may be efficiently diffused in the holder 330A, and radiated to the outside via the Peltier element 340 and the heat sink 341. Accordingly, the temperatures of the light sources (the first light source 321, the second light source 322, and the third light source 323) may be maintained uniform. In addition, according to the first modification example, the length of the wiring connecting the first light source 321 and the substrate 350 is shortened, so that the occurrence of blunting of the rectangular wave of the pulse may be suppressed, and the light emission of the light sources may be controlled with high accuracy.

In addition, in the first modification example, since the volume of the region $R_{21}$ is larger than the volume of the region $R_{11}$, heat uniformity is better than that in the configuration (refer to FIG. 4) according to the above-described embodiment.

Figure 10:
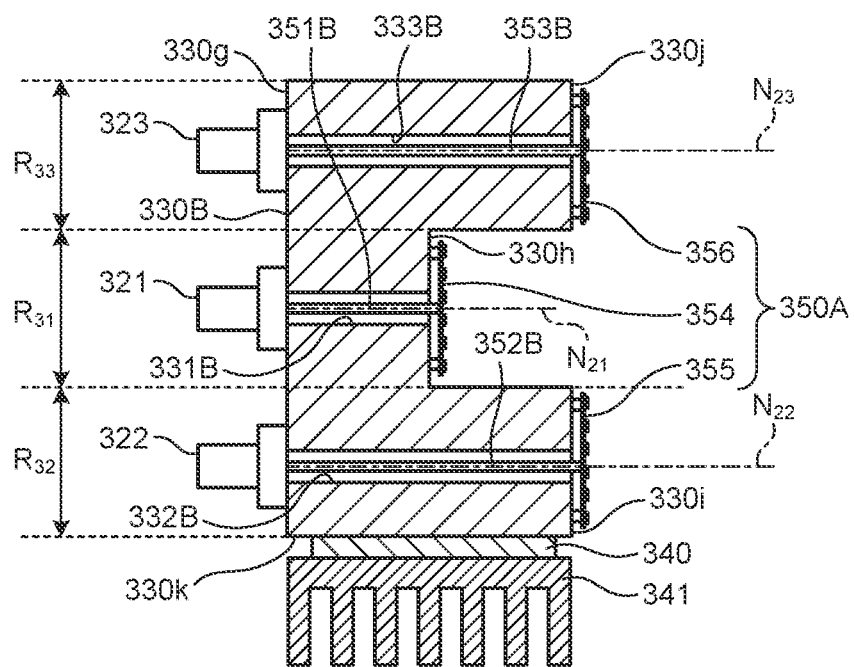
FIG. 10 is a view describing a configuration of main parts of a light source apparatus of a light source device provided in an endoscope system according to a second modification example of the embodiment.

Next, a second modification example of the embodiment will be described with reference to FIG. 10. FIG. 10 is a view describing a configuration of main parts of a light source apparatus of a light source device provided in an endoscope system according to the second modification example of the embodiment. The endoscope system according to the second modification example has the same configuration, except that the configurations of the holder and the substrate in the light source device 3 of the endoscope system 1 described above are changed. Hereinafter, configurations of a holder and a substrate which are different from the configurations of the above-described embodiment will be described. Hereinafter, the configurations of the holder and the substrate in the first light source apparatus 311B will be described, and similar to the embodiment, the same holder and substrate may also be arranged in the second light source apparatus 311G and the third light source apparatus 311R.

The first light source apparatus 311B according to the second modification example includes the first light source 321 formed of a set of three light sources (light sources 320A to 320C); the second light source 322 formed of a set of three light sources (light sources 321A to 321C); the third light source 323 formed of a set of three light sources (light sources 322A to 322C); a holder 330B that holds each light source; the Peltier element 340 attached to the holder 330B; the heat sink 341; and a substrate 350A on which a circuit that controls the light emission of each light source is formed.

The holder 330B is a prismatic member having a recessed bottom surface. The first light source 321, second light source 322, and the third light source 323 are arranged on the same surface 330g of the holder 330B. The surface 330g is a surface located opposite a recessed portion of a recess. The second modification example has a configuration in which optical characteristics are prioritized by disposing the first light source 321 at the center of the surface 330g.

In addition, the holder 330B is provided with a first communication portion 331B that allows the surface 330g on which the first light source 321 is arranged and a surface 330h facing the substrate 350A (first substrate 354 to be described later) to communicate with each other, a second communication portion 332B that allows the surface 330g on which the second light source 322 is arranged and a surface 330i facing the substrate 350A (second substrate 355 to be described later) to communicate with each other, and a third communication portion 333B that allows the surface 330g on which the third light source 323 is arranged and a surface 330j facing the substrate 350A (third substrate 356 to be described later) to communicate with each other.

Here, the surface 330h is a surface that forms a bottom portion of the recessed portion of the recess. In addition, the surface 330i is a distal end surface forming an aperture of the recessed portion of the recess, and is a distal end surface located on a surface 330g side. The surface 330j is a distal end surface forming the aperture of the recessed portion of the recess, and is a distal end surface located opposite the surface 330g side.

The surfaces 330h to 330j intersect with normal lines $N_{21}$ to $N_{23}$ of the surface 330g. The normal line $N_{21}$ is a straight line passing through the optical axis (center of the arrangement position) of the light source 321A (or the light source 321B or 321C) and extending perpendicular to the surface 330g. The normal line $N_{22}$ is a straight line passing through the optical axis (center of the arrangement position) of the light source 322A (or the light source 322B or 322C) and extending perpendicular to the surface 330g. The normal line $N_{23}$ is a straight line passing through the optical axis (center of the arrangement position) of the light source 323A (or the light source 323B or 323C) and extending perpendicular to the surface 330g. The normal lines $N_{21}$ to $N_{23}$ are parallel to each other.

The first communication portions 331B each have a hole shape extending in a direction of the normal line $N_{21}$ of the surface 330g. Similarly, the second communication portions 332B each have a hole shape extending in a direction of the normal line $N_{22}$ of the surface 330g. The third communication portions 333B each have a hole shape extending in a direction of the normal line $N_{23}$ of the surface 330g.

A first wiring 351B connecting the first light source 321 and the substrate 350 is inserted into the first communication portion 331B. A second wiring 352B connecting the second light source 322 and the substrate 350 is inserted into the second communication portion 332B. A third wiring 353B connecting the third light source 323 and the substrate 350 is inserted into the third communication portion 333B.

In the holder 330B, the surface 330h is located closer to a surface 330g side than the surfaces 330i and 330j (refer to FIG. 10). For this reason, the length of the first communication portion 331B in the direction of the normal line $N_{21}$ (central axis direction of the hole) is shorter than the length of the second communication portion 332B in the direction of the normal line $N_{22}$.

From the length of the first communication portion 331B, the length of the second communication portion 332B, and the disposition of the substrate 350A, the length of the first wiring 351B connecting the first light source 321 and the substrate 350A (first substrate 354) is shorter than the length of the second wiring 352B. Also in the second modification example, since the first wiring 351B is shorter than the second wiring 352B, and the third wiring 353B, the influence of blunting is small.

In the first light source apparatus 311B, when the holder 330B is divided into three equal sections by planes parallel to a surface 330k, on which the Peltier element 340 and the heat sink 341 are provided, in a direction orthogonal to the planes, the volume of a region $R_{31}$ in which the first light source 321 is arranged is smaller than the volume of a region $R_{32}$ in which the second light source 322 is arranged.

Heat that has diffused in the region $R_{31}$ is absorbed by the Peltier element 340 via the regions $R_{32}$. In addition, heat that has diffused in a region $R_{33}$ is absorbed by the Peltier element 340 via the regions $R_{31}$ and $R_{32}$.

The heat absorption side of the Peltier element 340 is disposed on the surface 330k of the holder 330B, and the heat generation side thereof is disposed on the heat sink 341. Heat generated by the first light source 321, the second light source 322, and the third light source 323 is absorbed by the Peltier element 340 via the holder 330B, and is released to the outside via the heat sink 341. Due to the shape of the holder 330B, the volume in which heat is diffused is smaller on the first light source 321 side than on the second light source 322 side.

The substrate 350A includes the first substrate 354 that faces the surface 330h and is connected to the first wiring 351B; the second substrate 355 that faces the surface 330i and is connected to the second wiring 352B; and the third substrate 356 that faces the surface 330j and is connected to the third wiring 353B. The first substrate 354, the second substrate 355, and the third substrate 356 are electrically connected to the light source driver 310 individually or collectively.

In the second modification example described above, in the holder 330B having a prismatic shape and having the recessed bottom surface, the first light source 321 is disposed opposite the surface 330h forming the bottom portion of the recessed portion of the recess, and the second light source 322 is disposed opposite the distal end surface (surface 330i) forming the aperture of the recessed portion of the recess. In the second modification example, due to the shape of the holder 330B and the order of arrangement of the light sources described above, heat generated by each light source may be efficiently diffused in the holder 330B, and radiated to the outside via the Peltier element 340 and the heat sink 341. Accordingly, the temperatures of the light sources may be maintained uniform. In addition, according to the second modification example, the length of the wiring connecting the first light source 321 and the first substrate 354 is shortened, so that the occurrence of blunting of the rectangular wave of the pulse nay be suppressed, and the light emission of the light sources may be controlled with high accuracy.

Incidentally, in the second modification example, the Peltier element 340 or the heat sink 341 may be provided on a surface opposite the surface 330k, namely, a surface on which the third light source 323 is arranged.

Figure 11:
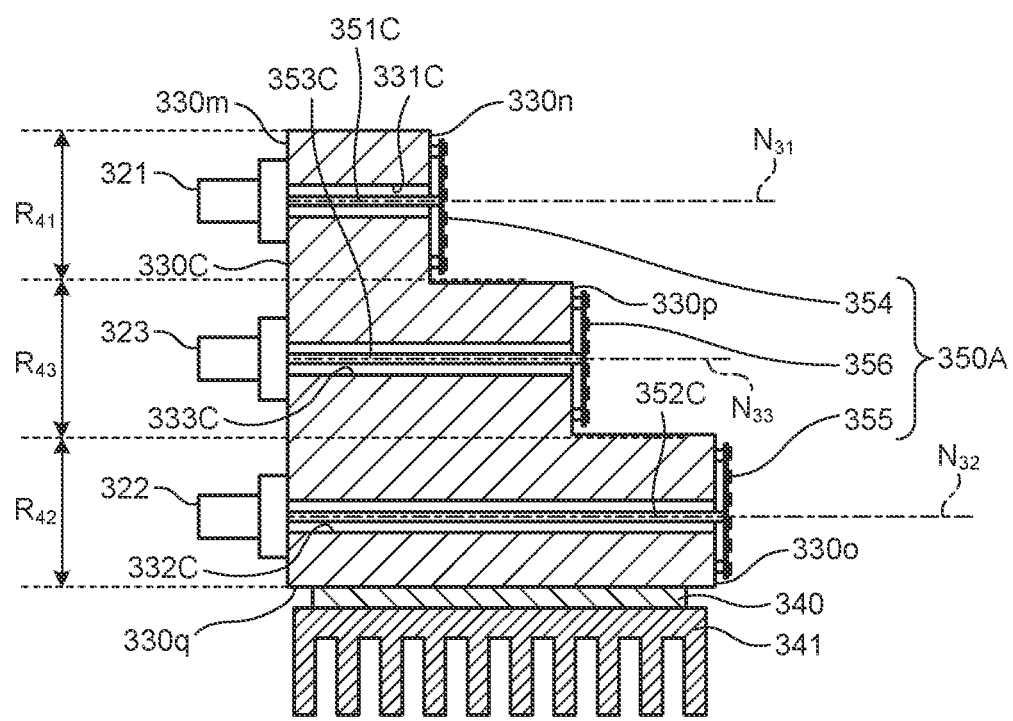
FIG. 11 is a view describing a configuration of main parts of a light source apparatus of a light source device provided in an endoscope system according to a third modification example of the embodiment.

Next, a third modification example of the embodiment will be described with reference to FIG. 11. FIG. 11 is a view describing a configuration of main parts of a light source apparatus of a light source device provided in an endoscope system according to the third modification example of the embodiment. The endoscope system according to the third modification example has the same configuration, except that the configuration of the holder in the second modification example described above is changed. Hereinafter, a configuration of a holder which is different from the configuration of the above-described second modification example will be described. Hereinafter, the configuration of the holder in the first light source apparatus 311B will be described, and similar to the embodiment, the same holder may also be arranged in the second light source apparatus 311G and the third light source apparatus 311R.

The first light source apparatus 311B according to the third modification example includes the first light source 322 formed of a set of three light sources (light sources 320A to 320C); the second light source 322 formed of a set of three light sources (light sources 321A to 321C); the third light source 323 formed of a set of three light sources (light sources 322A to 322C); a holder 330C that holds each light source; the Peltier element 340 attached to the holder 330C; the heat sink 341; and the substrate 350A on which a circuit that controls the light emission of each light source is formed.

The holder 330C is a solid member (excluding through-holes to be described later) having a step shape. The first light source 321, second light source 322, and the third light source 323 are arranged on the same surface 330m of the holder 330C. The surface 330m is a surface forming a surface portion different from a surface portion in which a plurality of step portions are formed. The holder 330C has a three-stage step shape.

In addition, the holder 330C is provided with a first communication portion 331C that communicates between the surface 330m on which the first light source 321 is arranged and a surface 330n facing the first substrate 354 of the substrate 350A, a second communication portion 332C that communicates between the surface 330m on which the second light source 322 is arranged and a surface 330o facing the second substrate 355, and a third communication portion 333C that communicates between the surface 330m on which the third light source 323 is arranged and a surface 330p facing the third substrate 356.

Here, the surface 330n is a surface corresponding to a riser of a stage forming the uppermost stage. In addition, the surface 330o is a surface corresponding to a riser of a stage forming the lowermost stage. The surface 330p is a surface corresponding to a riser of a stage forming a middle stage.

The surfaces 330n to 330p intersect with normal lines $N_{31}$ to $N_{33}$ of the surface 330m. The normal line $N_{31}$ is a straight line passing through the optical axis (center of the arrangement position) of the light source 321A (or the light source 321B or 321C) and extending perpendicular to the surface 330m. The normal line $N_{32}$ is a straight line passing through the optical axis (center of the arrangement position) of the light source 322A (or the light source 322B or 322C) and extending perpendicular to the surface 330m. The normal line $N_{33}$ is a straight line passing through the optical axis (center of the arrangement position) of the light source 323A (or the light source 323B or 323C) and extending perpendicular to the surface 330m. The normal lines $N_{31}$ to $N_{33}$ are parallel to each other.

The first communication portions 331C each have a hole shape extending in a direction of the normal line $N_{31}$ of the surface 330m. Similarly, the second communication portions 332C each have a hole shape extending in a direction of the normal line $N_{32}$ of the surface 330m. The third communication portions 333C each have a hole shape extending in a direction of the normal line $N_{33}$ of the surface 330m.

A first wiring 351C connecting the first light source 321 and the substrate 350A is inserted into the first communication portion 331C. A second wiring 352C connecting the second light source 322 and the substrate 350A is inserted into the second communication portion 332C. A third wiring 353C connecting the third light source 323 and the substrate 350A is inserted into the third communication portion 333C.

In the holder 330C, the surface 330n is located closer to a surface 330m side than the surfaces 330o and 330p (refer to FIG. 11). For this reason, the length of the first communication portion 331C in the direction of the normal line $N_{31}$ (central axis direction of the hole) is shorter than the length of the second communication portion 332C in the direction of the normal line $N_{32}$ and the length of the third communication portion 333C in the direction of the normal line $N_{33}$.

From the length of the first communication portion 331C, the length of the second communication portion 332C, and the disposition of the substrate 350A, the length of the first wiring 351C connecting the first light source 321 and the first substrate 354 is shorter than the length of the second wiring 352C. Also in the third modification example, since the first wiring 351C is shorter than the second wiring 352C, and the third wiring 353C, the influence of blunting is small.

In the first light source apparatus 311B, the first light source 321, the third light source 323, and the second light source 322 are disposed in order of distance from a surface 330q on which the Peltier element 340 and the heat sink 341 are provided. This order is the decreasing order of the dimming resolution. In addition, when the holder 330C is divided into three equal sections by planes parallel to the surface 330q in a direction orthogonal to the planes, the volume of a region $R_{41}$ in which the first light source 321 is arranged is smaller than the volume of a region $R_{42}$ in which the second light source 322 is arranged.

Heat that has diffused in the region $R_{41}$ is conducted to the Peltier element 340 via the regions $R_{43}$ and $R_{42}$. In addition, heat that has diffused in the region $R_{43}$ is conducted to the Peltier element 340 via the region $R_{42}$.

The heat absorption side of the Peltier element 340 is disposed on the surface 330q of the holder 330B, and the heat generation side thereof is disposed on the heat sink 341. The surface 330q is a surface forming a surface portion that is located on a lowermost stage side among surface portions different from a surface portion in which a plurality of step portions are formed. Heat generated by the first light source 321, the second light source 322, and the third light source 323 is conducted to the Peltier element 340 via the holder 330C, and is released to the outside via the heat sink 341. At this time, the heat quantity generated by the first light source 321 is smaller than the heat quantity generated by the second light source 322 due to the light quantity to be emitted. Due to the shape of the holder 330C, the volume in which heat is diffused is smaller on the first light source 321 side than on the second light source 322 side.

In the third modification example described above, in the holder 330C having a step shape, the first light source 321 is arranged opposite the surface 330n corresponding to the riser of the uppermost stage, and the second light source 322 is disposed opposite the surface 330o corresponding to the riser of the lowermost stage. In the third modification example, due to the shape of the holder 330C and the order of arrangement of the light sources described above, heat generated by each light source may be efficiently diffused in the holder 330C, and radiated to the outside via the Peltier element 340 and the heat sink 341. Accordingly, the temperatures of the light sources may be maintained uniform. In addition, according to the third modification example, the length of the wiring connecting the first light source 321 and the first substrate 354 is shortened, so that the occurrence of blunting of the rectangular wave of the pulse may be suppressed, and the light emission of the light sources may be controlled with high accuracy.

Figure 12:
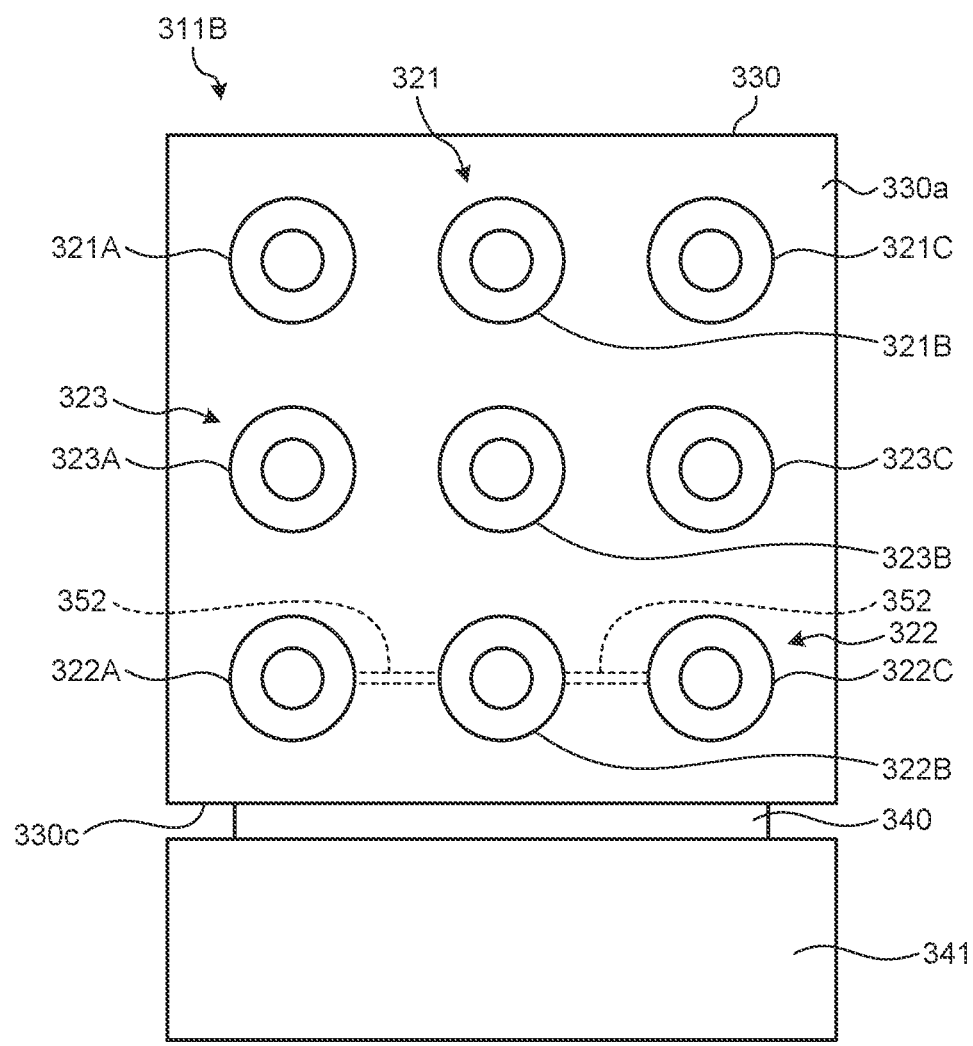
FIG. 12 is a view describing a configuration of a light source apparatus of a light source device provided in an endoscope system according to a fourth modification example of the embodiment.

Next, a fourth modification example of the embodiment will be described with reference to FIG. 12. FIG. 12 is a view describing a configuration of a light source apparatus of a light source device provided in an endoscope system according to the fourth modification example of the embodiment. The endoscope system according to the fourth modification example includes the same components as those of the endoscope system 1 described above. Hereinafter, different modes from those of the above-described embodiment will be described. Hereinafter, the configuration of the holder in the first light source apparatus 311B will be described, and similar to the embodiment, the same holder may also be arranged in the second light source apparatus 311G and the third light source apparatus 311R.

In the first light source apparatus 311B according to the fourth modification example, the light sources 322A to 322C forming the second light source 322 are connected in series to each other between the holder 330 and the substrate 350. Specifically, between the holder 330 and the substrate 350, the second wirings 352 extending from the respective light sources (light sources 322A to 322C) and extending from the respective second communication portions 332 are strung, and a wiring in which a group of the second wirings 352 are strung is connected to the substrate 350.

In the fourth modification example described above, similar to the embodiment, the Peltier element 340 and the heat sink 341 are provided on the surface 330c of the holder 330 having a triangular prismatic shape, and the first light source 321, the third light source 323, and the second light source 322 are arranged in decreasing order of the dimming resolution from the side distant from the surface 330c. According to the fourth modification example, the temperatures of the light sources (the first light source 321, the second light source 322, and the third light source 323) may be maintained uniform. In addition, according to the fourth modification example, the length of the wiring connecting the first light source 321 and the substrate 350 is shortened, so that the occurrence of blunting of the rectangular wave of the pulse may be suppressed, and the light emission of the light sources may be controlled with high accuracy.

In addition, in the fourth modification example, the light sources 322A to 322C may be electrically regarded as one light source due to being strung, so that the light sources 322A to 322C may be used as one light source having a low dimming resolution (coarse), and a reduction in the size of a control circuit or a cost reduction may be realized.

Figure 13:
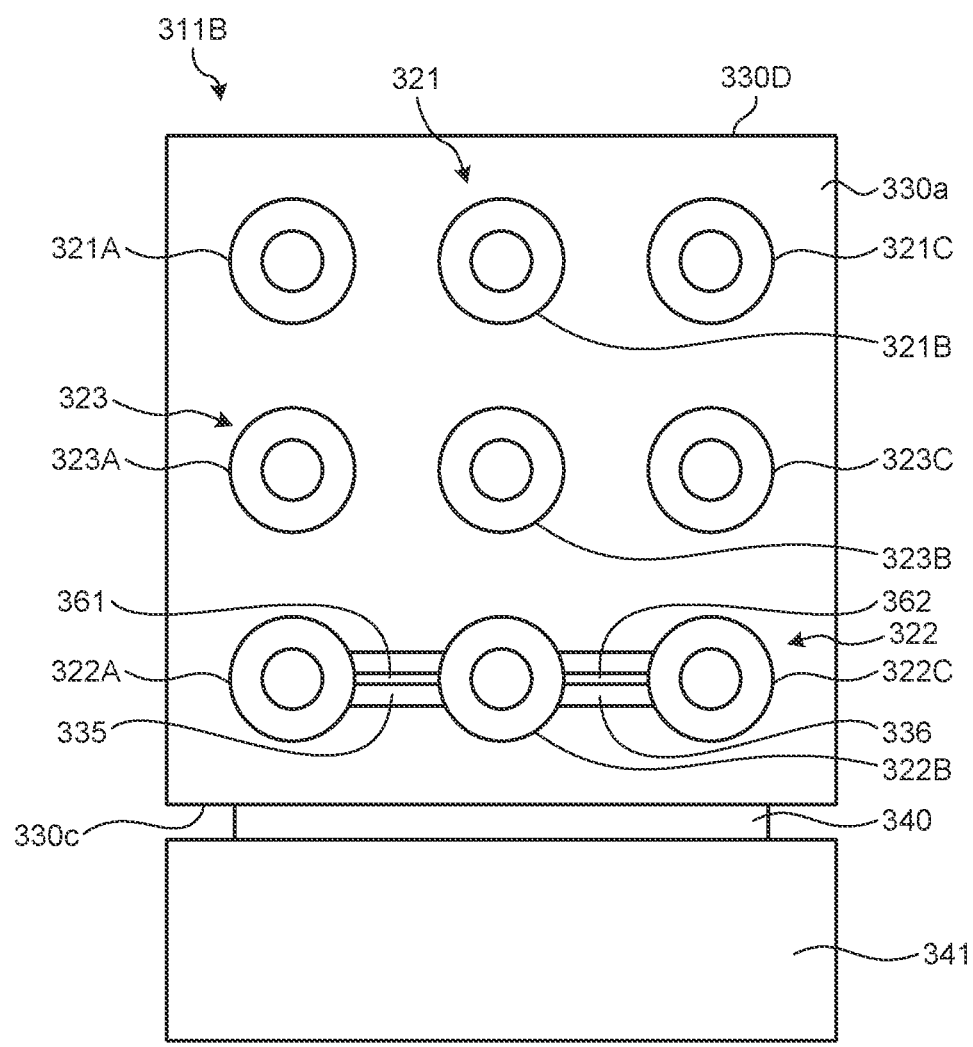
FIG. 13 is a view describing a configuration of a light source apparatus of a light source device provided in an endoscope system according to a fifth modification example of the embodiment.

Next, a fifth modification example of the embodiment will be described with reference to FIG. 13. FIG. 13 is a view describing a configuration of a light source apparatus of a light source device provided in an endoscope system according to the fifth modification example of the embodiment. The endoscope system according to the fifth modification example has the same configuration, except that the configuration of the holder in the light source device 3 of the endoscope system 1 described above is changed. Hereinafter, a configuration of a holder which is different from the configuration of the above-described embodiment will be described. Hereinafter, the configuration of the holder in the first light source apparatus 311B will be described, and similar to the embodiment, the same holder may also be arranged in the second light source apparatus 311G and the third light source apparatus 311R.

The first light source apparatus 311B according to the fifth modification example includes the first light source 321 formed of a set of three light sources (light sources 320A to 320C); the second light source 322 formed of a set of three light sources (light sources 321A to 321C); the third light source 323 formed of a set of three light sources (light sources 322A to 322C); a holder 330D that holds each light source; the Peltier element 340 attached to the holder 330D; the heat sink 341; and the substrate 350 on which a circuit that controls the light emission of each light source is formed.

The holder 330D has the same shape as that of the holder 330 described above. In addition, in addition to the first communication portion 331, the second communication portion 332, and the third communication portion 333, connection grooves 333 and 336 extending between the second communication portions 332 adjacent to each other are formed in the holder 330D. Both end portions of each of the connection grooves 335 and 336 are connected to the second communication portion 332 (refer to FIG. 4).

In the first light source apparatus 311B according to the fifth modification example, the light sources 322A to 322C forming the second light source 322 are connected in series to each other through the connection grooves 335 and 336. Specifically, a wiring 361 connecting the light source 322A and light source 322B is disposed in the connection groove 335. In addition, a wiring 362 connecting the light source 322B and light source 322C is disposed in the connection groove 336. The connection grooves 335 and 336 have such a depth capable of accommodating the wirings 361 and 362, respectively.

In the first, light source apparatus 311B according to the fifth modification example, the second wiring 352 described above is not connected to the light source 322B located at the center among the light sources forming the second light source 322.

The second wiring 352 connected to the light source 322A and the second wiring 352 connected to the light source 322C are connected to the substrate 350.

In the fifth modification example described above, similar to the embodiment, the Peltier element 340 and the heat sink 341 are provided on the surface 330c of the holder 330D having a triangular prismatic shape, and the first light source 321, the third light source 323, and the second light source 322 are arranged in decreasing order of the dimming resolution from the side distant from the surface 330c. According to the fifth modification example, the temperatures of the light sources (the first light source 321, the second light source 322, and the third light source 323) may be maintained uniform. In addition, according to the fifth modification example, the length of the wiring connecting the first light source 321 and the substrate 350 is shortened, so that the occurrence of blunting of the rectangular wave of the pulse may be suppressed, and the light emission of the light sources may be controlled with high accuracy.

In addition, in the fifth modification example, the light sources 322A to 322C of the second light source 322 are directly connected to each other on the light source arrangement surface of the holder 330D, so that one second wiring 352 may be eliminated compared to the configuration according to the embodiment. Since the length of the wiring related to the second light source 322 does not shorten due to the elimination of the second wiring 352, the occurrence of blunting of the rectangular wave of the pulse may be more reliably suppressed.

Figure 14:
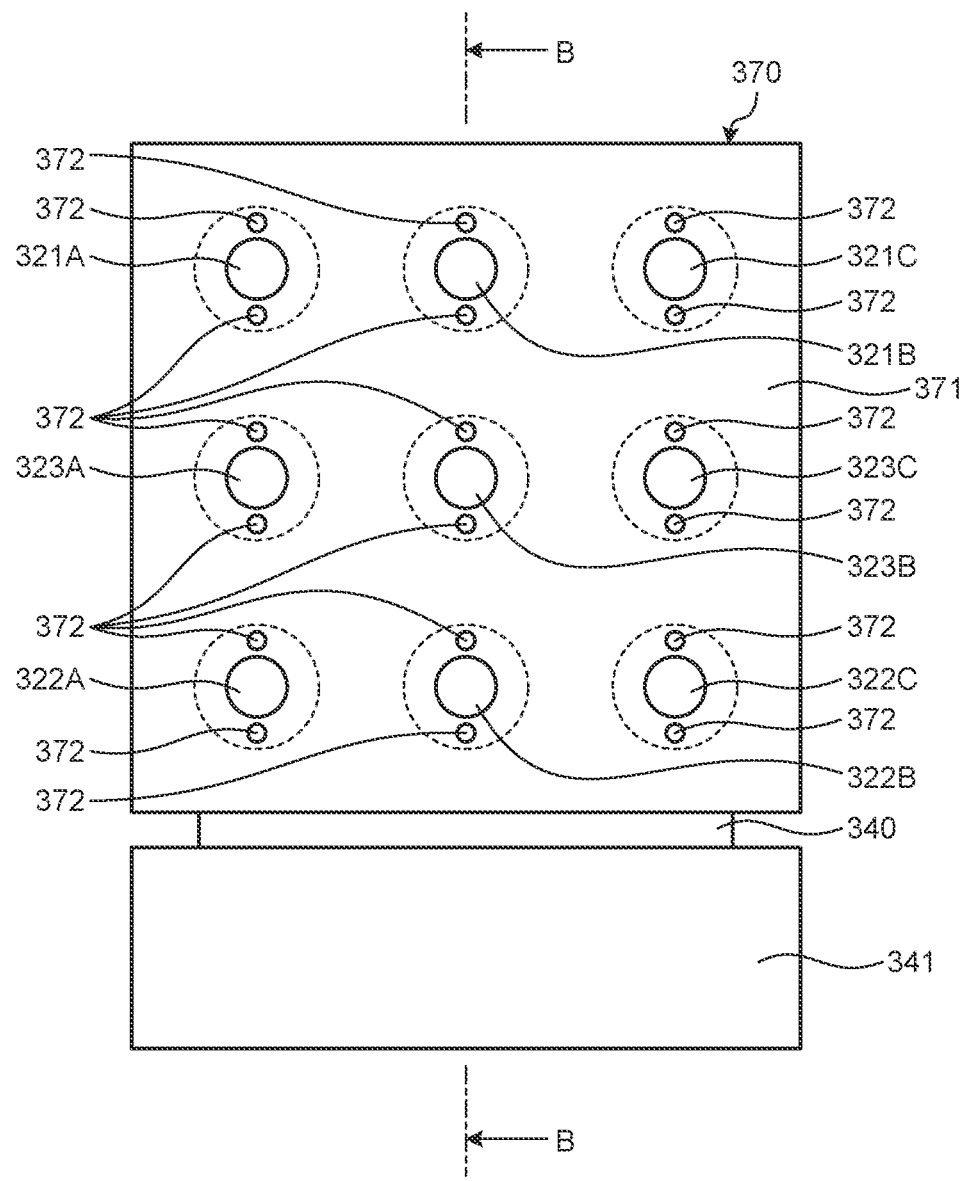
FIG. 14 is a view describing a configuration of a light source apparatus of a light source device provided in an endoscope system according to a sixth modification example of the embodiment.
Figure 15:
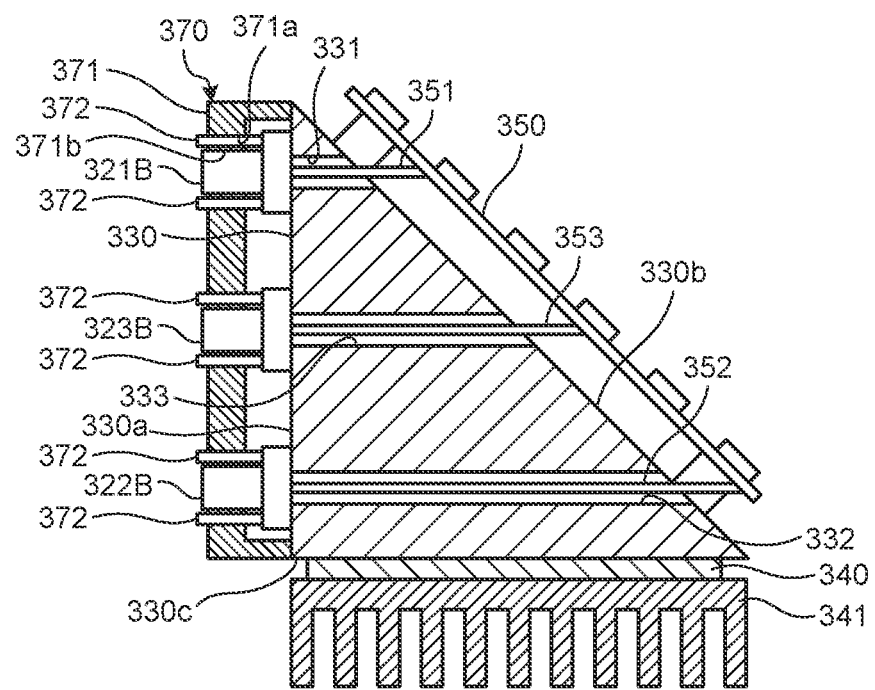
FIG. 15 is a cross-sectional view taken along line B-B illustrated in FIG. 14.

Next, a sixth modification example of the embodiment will be described with reference to FIGS. 14 and 15. FIG. 14 is a view describing a configuration of a light source apparatus of a light source device provided in an endoscope system according to the sixth modification example of the embodiment. FIG. 15 is a cross-sectional view taken along line B-B illustrated in FIG. 14. In the endoscope system according to the sixth modification example, the light source apparatus further includes a pressing member that presses each light source, in addition to the same configuration as that of the endoscope system 1 described above. Hereinafter, different configurations from the above-described embodiment will be described. Hereinafter, the configuration of the holder in the first light source apparatus 311B will be described, and similar to the embodiment, the same holder may also be arranged in the second light source apparatus 311G and the third light source apparatus 311R.

The first light source apparatus 311B according to the sixth modification example includes the first light source 321 formed of a set of three light sources (light sources 320A to 320C); the second light source 322 formed of a set of three light sources (light sources 321A to 321C); the third light source 323 formed of a set of three light sources (light sources 322A to 322C); the holder 330 that holds each light source; the Peltier element 340 attached to the holder 330; the heat sink 341; the substrate 350 on which a circuit that controls the light emission of each light source is formed; and a pressing member 370 that presses each light source.

The pressing member 370 includes a main body portion 371 attached to the holder 330, and a plurality of screws 372 that press the light source against the surface 330a of the holder 330. A first through-hole 371a through which the screw 372 penetrates and a second through-hole 371b through which an end portion on a light emission side of the light source penetrates are formed in the main body portion 371. In addition, the main body portion 371 is fixed to the holder 330 with screws or an adhesive not illustrated.

In the first light source apparatus 311B, each light source is individually crimped to the holder 330 by adjusting the amount of insertion of each of the screws 372 into the holder 330.

In the sixth modification example described above, similar to the embodiment, the Peltier element 340 and the heat sink 341 are provided on the surface 330c of the holder 330 having a triangular prismatic shape, and the first light source 321, the third light source 323, and the second light source 322 are arranged in decreasing order of the dimming resolution from the side distant from the surface 330c. According to the sixth modification example, the temperatures of the light sources (the first light source 321, the second light source 322, and the third light source 323) may be maintained uniform. In addition, according to the sixth modification example, the length of the wiring connecting the first light source 321 and the substrate 350 is shortened, so that the occurrence of blunting of the rectangular wave of the pulse may be suppressed, and the light emission of the light sources may be controlled with high accuracy.

In addition, in the sixth modification example, since the pressing member 370 is provided, and the light source is individually crimped to the holder 330 with each of the screws 372, even when a difference in thickness occurs due to production errors of each light source or the like, each light source may be reliably crimped to the holder 330.

The mode for implementing the present disclosure has been described so far; however, the present disclosure should not be limited solely by the above-described embodiment. The present disclosure may include various embodiments and the like that are not described here.

In addition, in the above-described embodiment, the arrangement positions of the Peltier element 340 and the heat sink 341 provided in the first light source apparatus 311B are not limited to the above-described positions. For example, the Peltier element 340 and the heat sink 341 may be provided on a side surface of the triangular prismatic shape of the holder 330. In addition, in the first light source apparatus 311B, a plurality of sets of the Peltier elements 340 and the heat sinks 341 may be arranged on the holder 330. In addition, the first light source apparatus 311B may be configured such that the Peltier element 340 is not provided and heat of the holder 330 is released to the outside only by the heat sink 341. These modification examples may also be applied to the second light source apparatus 311G and the third light source apparatus 311R, and may also be applied to the first to sixth modification examples in the same manner.

In addition, the above-described embodiment has been described as including three light sources (the first light source 321 to the third light source 323) of which the maximum light quantities to be emitted are different from each other; however, the present disclosure is not limited thereto. For example, a configuration may be adopted in which only the first light source 321 and the second light source 322 are provided, or a configuration may be adopted in which four or more light sources (fourth and above light sources) are provided.

In addition, in the above-described embodiment, each of the first light source 321 to the third light source 323 has been described as including three light sources; however, the present disclosure is not limited thereto. For example, a configuration may be adopted in which the first light source 321 includes one light source and the second light source 322 includes four light sources. In addition, in the above-described embodiment, the light source device 3 has been described as being formed separately from the endoscope 2; however, a configuration may be adopted in which the endoscope 2 is provided with the light source device, for example, a semiconductor laser is provided at a distal end of the endoscope 2. Further, the function of the processing device 4 may be added to the endoscope 2.

In addition, in the above-described embodiment, the light source device 3 has been described as being separate from the processing device 4; however, the light source device 3 and the processing device 4 may be integrated, for example, the light source unit 31 and the illumination control unit 32 may be provided inside the processing device 4.

In addition, in the above-described embodiment, the light source device 3 may be formed of LED light sources instead of semiconductor lasers. A configuration may be adopted in which a white light source (for example, a xenon lamp or a halogen lamp) is provided, a rotating filter is provided on an optical path of illumination light illuminated by the white light source, the rotating filter including three transmitting filters that transmit a red wavelength band, a green wavelength band, and a blue wavelength band, and the rotating filter is rotated to irradiate illumination light including the red, green, and blue wavelength bands.

In addition, in the above-described embodiment, the endoscope system according to the present disclosure has been described as the endoscope system 1 using the endoscope 2 that is soft and has a biological tissue or the like in the subject as an observation target; however, the present disclosure may also be applied to an endoscope system using a hard endoscope, an industrial endoscope for observing the characteristics of materials, a capsule-type endoscope, a fiberscope, or an optical endoscope such as an optical viewing tube in which a camera head is connected to an eyepiece.

As described above, the light source apparatus for an endoscope according to the present disclosure is useful for maintaining the temperatures of the light sources uniform and suppressing the occurrence of blunting of a pulse signal.

The present disclosure displays the effect of being capable of maintaining the temperature of the light sources uniform and suppressing the occurrence of blunting of a pulse signal.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. A light source apparatus comprising:
   a first light source;
   a second light source configured to emit light having a dimming resolution lower than a dimming resolution of the first light source;
   a holder configured to hold the first light source and the second light source on a first surface of the holder;
   a substrate provided to face a second surface of the holder, the second surface being different from the first surface, and a circuit configured to control driving of the first light source and the second light source being mounted on the substrate;
   a first wiring configured to electrically connect the first light source and the substrate; and
   a second wiring configured to electrically connect the second light source and the substrate,
   wherein a length of the first wiring is shorter than a length of the second wiring.

2. The light source apparatus according to claim 1, wherein the holder includes
   a first communication portion extending in a normal direction of the first surface to allow the first surface and the second surface to communicate with each other and into which the first wiring is inserted, and
   a second communication portion extending in the normal direction of the first surface to allow the first surface and the second surface to communicate with each other and into which the second wiring is inserted.

3. The light source apparatus according to claim 2, wherein
   the holder includes
      a first region in which the first light source is arranged and into which the first communication portion is inserted, and
      a second region in which the second light source is arranged and into which the second communication portion is inserted, and
   a volume of the first region is smaller than a volume of the second region.

4. The light source apparatus according to claim 2, wherein the first communication portion and the second communication portion are parallel to each other.

5. The light source apparatus according to claim 2, wherein a distance from a position of the first light source to the second surface in the normal direction is shorter than a distance from a position of the second light source to the second surface in the normal direction.

6. The light source apparatus according to claim 2, wherein a length of the first communication portion in the normal direction is shorter than a length of the second communication portion in the normal direction.

7. The light source apparatus according to claim 2, wherein
the second light source includes a plurality of light sources, and
the plurality of light sources are connected in series to each other, and are electrically connected to the substrate.

8. The light source apparatus according to claim 1, wherein the holder includes a heat radiator configured to release heat to an outside of the light source apparatus, the heat being generated by the first light source and the second light source and transferred via the holder, and the heat radiator is provided on a third surface different from the first surface and the second surface.

9. The light source apparatus according to claim 8, wherein the first light source and the second light source are disposed on the first surface in order according to a distance from the third surface.

10. The light source apparatus according to claim 8, wherein the holder has a triangular prismatic shape, and the second surface is inclined with respect to the first surface.

11. The light source apparatus according to claim 8, wherein the heat radiator includes at least a heat sink.

12. The light source apparatus according to claim 1, wherein the second light source is configured to emit a color component identical to a color component of the first light source.

13. An endoscope system comprising: an endoscope adapted to be inserted into a subject; and a light source apparatus configured to generate illumination light emitted from a distal end of the endoscope, the light source apparatus comprising: a first light source; a second light source configured to emit light having a dimming resolution lower than a dimming resolution of the first light source; a holder configured to hold the first light source and the second light source on a first surface of the holder; a substrate provided to face a second surface of the holder, the second surface being different from the first surface, and a circuit configured to control driving of the first light source and the second light source being mounted on the substrate; a first wiring configured to electrically connect the first light source and the substrate; and a second wiring configured to electrically connect the second light source and the substrate, wherein a length of the first wiring is shorter than a length of the second wiring.

* * * * *